United States Patent
Yu et al.

(10) Patent No.: US 11,965,187 B2
(45) Date of Patent: Apr. 23, 2024

(54) TARGETED DNA DEMETHYLATION METHOD, FUSION PROTEIN AND APPLICATION THEREOF PRELIMINARY CLASS

(71) Applicants: Guangzhou Medical University, Guangzhou (CN); GMU New Drug Development Co., Ltd., Guangzhou (CN)

(72) Inventors: Xi-Yong Yu, Guangzhou (CN); Yu-Guang Zhu, Guangzhou (CN); Ao Shen, Guangzhou (CN); Ling-Min Zhang, Guangzhou (CN); Ji-Shuo Chang, Guangzhou (CN)

(73) Assignees: GUANGZHOU MEDICAL UNIVERSITY, Guangzhou (CN); GMU NEW DRUG DEVELOPMENT CO., LTD., Guangzhou (CN)

(*) Notice: Subject to any disclaimer, the term of this patent is extended or adjusted under 35 U.S.C. 154(b) by 0 days.

(21) Appl. No.: 18/155,097

(22) Filed: Jan. 17, 2023

(65) Prior Publication Data
US 2023/0287374 A1    Sep. 14, 2023

Related U.S. Application Data

(63) Continuation of application No. PCT/CN2022/081136, filed on Mar. 30, 2022.

(30) Foreign Application Priority Data

Jan. 17, 2022 (CN) .......................... 202210050631.9

(51) Int. Cl.
*C12N 9/22* (2006.01)
*A61K 48/00* (2006.01)
*C12N 15/85* (2006.01)

(52) U.S. Cl.
CPC ............ *C12N 9/22* (2013.01); *A61K 48/0008* (2013.01); *A61K 48/005* (2013.01); *C12N 15/85* (2013.01); *C07K 2319/09* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2009/0305241 | A1* | 12/2009 | Fischer | C12N 9/0073 435/468 |
| 2017/0159073 | A1* | 6/2017 | Donohoue | C12N 9/22 |
| 2018/0237771 | A1* | 8/2018 | Kim | C07K 14/515 |

FOREIGN PATENT DOCUMENTS

| | | |
|---|---|---|
| CN | 103820452 A | 5/2014 |
| CN | 106520830 A | 3/2017 |

OTHER PUBLICATIONS

Devesa-Guerra et al. DNA Methylation Editing by CRISPRguided Excision of 5-Methylcytosine. Journal of Molecular Biology (2020) 432, 2204-2216 (Year: 2020).*
Yamada et al. Crystal Structure of the Minimal Cas9 from Campylobacter jejuni Reveals the Molecular Diversity in the CRISPR-Cas9 Systems. 2017 Molecular Cell 65, 1109-1121 (Year: 2017).*
Hong et al. The Carboxy-Terminal Domain of ROS1 is Essential for 5-Methylcytosine DNA Glycosylase Activity. J. Mol. Biol. (2014) 426, 3703-3712 (Year: 2014).*
Ren et al., A CRISPR/Cas9 toolkit for efficient targeted base editing to induce genetic variations in rice. Sci China Life Sci 60, 1-4 (Year: 2017).*
CNIPA, Notification of a First Office Action for CN202210050631. 9, Aug. 15, 2022.
Guangzhou Medical University (Applicant), Reply to Notification of a First Office Action for CN202210050631.9, w/ (allowed) replacement claims, Sep. 19, 2022.
CNIPA, Notification to grant patent right for invention in CN202210050631.9, Nov. 9, 2022.

* cited by examiner

*Primary Examiner* — Celine X Qian
*Assistant Examiner* — Tiffany Nicole Grooms
(74) *Attorney, Agent, or Firm* — Zhigang Ma

(57) ABSTRACT

A targeted DNA demethylation method (Mini-CRISD) and a fusion protein used in the method are provided. The Mini-CRISD method can targets delivery of demethylation activity through engineered miniature dCjCas9 to deliver engineered miniature ROS1 demethylation effector to specific DNA sequences and/or specific genomic locations (such as CpG islands) to achieve targeted demethylation of specific DNA.

9 Claims, 7 Drawing Sheets

Specification includes a Sequence Listing.

TARGETED DNA DEMETHYLATION METHOD, FUSION PROTEIN AND APPLICATION THEREOF PRELIMINARY CLASS

TECHNICAL FIELD

The disclosure relates to the field of biotechnologies, and more particularly to a targeted DNA demethylation method, a fusion protein and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 22059THXT-USP1-SL.xml. The XML file is 38,918 bytes; is created on Jan. 12, 2023; and is being submitted electronically via EFS-Web.

BACKGROUND

DNA methylation is the most common form of DNA modification, which is usually covalently linked to a methyl group at the carbon-5 position of cytosine, resulting in the conversion of cytosine (C) to 5-methylcytosine (5 mC). DNA methylation leads to changes in chromatin structure and the ability of DNA to bind to protein, thereby affecting gene expression and genetic traits. DNA methylation is reversible, usually methylation inhibits gene expression, while demethylation promotes gene expression. Therefore, methylation and demethylation regulate gene expression without changing DNA sequence, which is one of the most common types of epigenetic regulation. The DNA methylation in eukaryotes usually occurs at the CpG islands in the genome (CpG islands refer to certain fragments of the genome rich in CG dinucleotides, mainly located in promoter and exon regions of genes). Correct DNA methylation is closely related to growth and development, physiological status, etc. Wrong DNA methylation can lead to abnormal growth and development and promote the occurrence and development of cancer. For example, Ras association domain family 1A (RASSF1A) is a typical tumor suppressor gene that encodes a protein that inhibits tumor formation by inhibiting Ras activation. Loss of RASSF1A expression due to methylation of the promoter region of RAS gene is a common event in human tumors and methylation inactivation of RASSF1A has been found in nearly 40 different cancers. As one of the cancers with the highest incidence rate and mortality in the world, lung cancer, RASSF1A promoter hypermethylation is detected in 100% of small cell lung cancer (SCLC), 63% of non-small cell lung cancer (NSCLC), and 30% of primary NSCLC, but not in normal lung epithelial cells. It can be seen that the inactivation of tumor suppressor genes caused by promoter hypermethylation of the tumor suppressor genes is one of common characteristics of various tumors. Based on this phenomenon, small molecule inhibitors of DNA methylation have been applied to the clinical treatment of many cancers. However, small molecule inhibitors are non-selective demethylation, resulting in abnormal activation of a large number of originally silent genes. Therefore, if a targeted DNA demethylation technology can be developed, it will be an important development direction of cancer precision medicine to specifically improve the expression of the tumor suppressor genes by targeting the promoter of the tumor suppressor genes. Similarly, targeted DNA demethylation can also be applied to the treatment of other diseases with abnormal DNA methylation, which will have wide and huge clinical effects.

DNA methylation is widespread in prokaryotes and eukaryotes. DNA demethylation in eukaryotes includes two ways, passive and active. Passive demethylation refers to that after the inactivation of DNA methyltransferase (DNMT), newly replicated DNA cannot be methylated, and the original 5 mC gradually decreases with cell division and replication. For active demethylation, animals and plants adopt different strategies. Animals use ten-eleven translocation (TET)-dioxygenase (including TET1, TET2 and TET3) to oxidize 5 mC into a series of derivatives. On the one hand, these derivatives cannot be recognized by DNMT and thus cannot maintain the methylation state, and on the other hand, thymine DNA glycosylase (TDG) will cut off these oxidation derivatives and realize demethylation through base excision repair (BER). In plants, DEMETER (DME) family DNA glycosidase (including repressor of silencing 1 abbreviated as ROS1, DEMETER-like 2 abbreviated as DML2, DEMETER-like 3 abbreviated as DML3) is used to directly recognize and remove 5 mC, and then demethylation is completed through BER.

At present, demethylation technology can be divided into two categories, non-targeted and targeted. Non-targeted methods mainly use small molecule inhibitors of DNA methylation, such as 5-Azacytidine (azacytidine, Vidaza), 5-Aza-2'-deoxycytidine (5-aza-2'-deoxycytidine, decitabine), and small interfering RNA (siRNA) gene silencing for DNMT. Targeted methods mainly involve fusion expression of one or more demethylation effectors on the basis of systems with DNA-targeting ability, such as zinc finger proteins (ZNFs), transcription activator-like effectors (TALEs), clustered regularly interspaced short palindromic repeat (CRISPR), so as to achieve the purpose of demethylation of specific DNA sequences. The demethylation effectors currently used include full-length TET1, truncated TET1 (TET1-catalytic domain abbreviated as TET1-CD), and full-length ROS1.

Targeted DNA technology using CRISPR has developed most rapidly. CRISPR system includes two key elements: a single guide RNA (sgRNA) and a CRISPR associated endonuclease (Cas). Cas is diverse in nature. Cas9 is currently the most widely used type in genetic engineering, and Cas9 can be derived from different bacteria. The sgRNA consists of a skeleton sequence (also referred to as a scaffold) necessary for binding to Cas9 and a recognition sequence (also referred to as a targeting sequence) recognizing a target DNA. By changing the recognition sequence, different targets on DNA or different target DNA can be selected. After sgRNA and Cas9 form a compound in vitro or in vivo, sgRNA guides Cas9 to bind to specific DNA targets and cleaves DNA. The nuclease cleavage activity of Cas9 depends on two domains, RuvC and HNH, which are respectively responsible for cleaving two strands of DNA. Through engineering modification of Cas9, nuclease inactivated Cas9 that lacks cleavage activity and still has the ability to target nuclease inactivation, Cas9 (dead Cas9, dCas9), can be obtained. The specificity of CRISPR targeting DNA is determined by two aspects, one is the base pairing between the sgRNA recognition sequence and the DNA target sequence, the other is the combination of Cas9 and a specific short DNA sequence. The specific short DNA sequence is usually at the 3' end of the DNA target sequence, which is called protospacer adjacent motif (PAM). Cas9 from different sources identify different PAM sequences. At present, the most commonly used Cas9 is derived from *Streptococcus pyogenes* (SpCas9), which contains 1368 amino acids, and the PAM sequence is 5'-NGG-3'. Compared with the SpCas9, the newly discovered Cas9 from *Campylobacter jejuni* (CjCas9) contains 984 amino acids, which is the smallest size of Cas9 found in nature. The PAM sequence of CjCas9 is 5'-NNNVYRAC-3', 5'-ACA-3', or 5'-NNNNYRAC-3'. Studies have shown that that CjCas9 has the same excellent gene editing potential as SpCas9.

At present, the developed DNA demethylation technologies have their own shortcomings. For non-targeted demethylation, non-specificity reduces the methylation level of the whole genome, and a large number of genes will be abnormally expressed, which seriously restricts its practical application. There are three main limitations of targeted demethylation, including low targeting, low specificity, and excessive fusion protein. For example, compared with CRISPR, ZNFs and TALEs not only need to specifically design each DNA target, but also have an "off-target" binding to the genome. At present, the most commonly used demethylation effector is full-length or truncated TET1, but the 5 mC derivative produced in the process of TET1 demethylation also carries epigenetic information, which will cause additional epigenetic effects in the process of demethylation. The amino acid sequence of the most commonly used SpCas9 and demethylation effector are both long, which makes the insertion fragment used for fusion expression of the two on the expression vector too long, while the commonly used gene therapy virus vectors (lentivirus, adeno-associated virus, etc.) have a size limit on the exogenous insertion fragment, which affects the packaging and the in vivo application of the virus vector, and thus it is difficult to achieve demethylation gene therapy based on virus delivery.

In order to overcome the above shortcomings, a new targeted DNA demethylation technique is developed in the disclosure, namely Miniature CjCas9-ROS1 Induced Specific Demethylation (abbreviated as Mini-CRISD). Compared with the existing art, the Mini-CRISD is based on a CRISPR-CjCas9 system, which ensures the targeting. The miniature CjCas9 protein and the demethylation effector ROS1 are used to facilitate the demethylation gene therapy based on virus delivery. In addition, 5 mC series derivatives will not be produced during demethylation, which will not cause additional epigenetic signals.

SUMMARY

The purpose of the disclosure is to provide a targeted DNA demethylation method (miniature CjCas9-ROS1 induced specific demethylation abbreviated as Mini-CRISD) and a fusion protein used in the method.

The Mini-CRISD method of the disclosure can realize targeted demethylation on specific DNA through target delivery of demethylation activity by engineered miniature *Campylobacter jejuni* clustered regularly interspaced short palindromic repeat associated endonuclease 9 (CjCas9) to deliver engineered miniature repressor of silencing 1 (ROS1) demethylation effector to specific DNA sequences and/or specific genomic positions (such as CpG islands).

In a first aspect of the disclosure, a fusion protein is provided, which includes a truncated nuclease inactivated CjCas9 (also referred to as dCjCas9ΔHNH) and a truncated ROS1 (also referred to as ROS1ΔN) connected by an intermediate sequence including a linker. The truncated CjCas9 (dCjCas9ΔHNH) is an amino acid fragment obtained by removing amino acids at positions 481-640 of a CjCas9 protein, connecting remaining amino acids with a linker, and performing D8A point mutation (the $8^{th}$ amino acid is mutated from aspartic acid abbreviated as D to alanine abbreviated as A). The truncated ROS (ROS1ΔN) is an amino acid fragment obtained by removing amino acids at positions 1-509 and 628-855 of a ROS1 protein and connecting remaining amino acids with a linker, and an amino acid at position 971 of the ROS1 protein is aspartic acid (also abbreviated as Asp).

In a second aspect of the disclosure, a nucleotide sequence encoding the fusion protein is provided, or a nucleotide sequence encoding the same amino acids of the fusion protein with a plurality of nucleotide mutations is provided. For example, the above nucleotide sequences encode the same amino acid sequence due to codon optimization or codon degeneracy.

In a third aspect of the disclosure, an expression vector capable of expressing the fusion protein is provided.

In a fourth aspect of the disclosure, a kit for targeted DNA demethylation is provided, which includes an expression vector capable of expressing the fusion protein or the fusion protein.

In a fifth aspect of the disclosure, a targeted DNA demethylation method is provided, including the following steps:

step S1, constructing an expression vector expressing the fusion protein;

step S2, obtaining a sgRNA sequence, where the sgRNA sequence includes a skeleton sequence capable of combining with the CjCas9ΔHNH (truncated CjCas9) and a recognition sequence completely complementary to a target sequence on a target DNA; and step S3, introducing the expression vector and the sgRNA sequence into a target containing target DNA, and performing targeted demethylation.

In a sixth aspect of the disclosure, applications of the fusion protein or the expression vector are provided.

Specifically, the fusion protein or the expression vector is applied to induce targeted DNA demethylation in vivo and/or ex vivo and/or in vitro.

The fusion protein or the expression vector is applied to prepare a medicine for cancer treatment based on targeted DNA demethylation.

The fusion protein or the expression vector is applied to prepare a medicine for treatment of diseases caused by abnormal DNA methylation.

In a seventh aspect of the disclosure, a fusion control protein is provided, which includes a truncated CjCas9 (also referred to as dCjCas9ΔHNH) and a truncated ROS1 (also referred to as ROS1ΔN) connected by an intermediate sequence including a linker. The truncated CjCas9 is an amino acid fragment obtained by removing amino acids at positions 481-640 of a CjCas9 protein, connecting remaining amino acids with a linker, and performing D8A point mutation (the 8th amino acid is mutated from D to A). The truncated ROS1 (ROS1ΔN) is an amino acid fragment obtained by removing amino acids at positions 1-509 and 628-855 of a ROS1 protein and connecting remaining amino acids with a linker, and an amino acid at position 971 of the ROS1 protein is not aspartic acid (Asp).

The targeted DNA demethylation method (Mini-CRISD) of the disclosure is the first time to use the truncated dCjCas9 as a DNA targeting tool, and also the first time to apply the truncated ROS1 to DNA demethylation, and also the first time to combine the truncated dCjCas9 and the truncated ROS1 after appropriate treatment to apply them to targeted DNA demethylation. Compared with the prior art, the advantages of the Mini-CRISD of the disclosure mainly include three aspects, genetic regulation, molecular technology, and gene targeting. (1) Regarding to the advantages of genetic regulation, ROS1 glucosidase from plants does not produce 5 mC derivatives in the process of demethylation, which avoids the problem of generating 5 mC derivatives and introducing additional genetic signals in the current method of using demethylation effectors from animals such as ten-eleven translocation 1 (TET1). (2) Regarding to the advantages of molecular technology, Mini-CRISD has a brand-new sequence design, which has smaller genetic sequence and higher activity compared with the clustered regularly interspaced short palindromic repeat (CRISPR) system currently in use, Mini-CRISD has smaller gene sequences and higher activity, so that the expression vector has a smaller size, and the demethylation gene therapy based on viral delivery, which is difficult to achieve due to the size of the vector, is possible. (3) Regarding to the advantage of gene targeting, based on CRISPR principle, Mini-CRISD has better targeting effect and lower miss rate compared with other targeting systems such as zinc finger proteins (ZNFs), transcription activator-like effectors (TALEs). Mini-CRISD can target the promoter region of genes, realize targeted demethylation of methylation genes, improve the expression of target genes, and the entire demethylation process will not cause additional epigenetic changes. The Mini-CRISD of the disclosure provides a new method for gene therapy induced in vivo and/or ex vivo and/or in vitro for various diseases with abnormal DNA methylation.

DETAILED DESCRIPTION OF EMBODIMENTS

Figure 1:
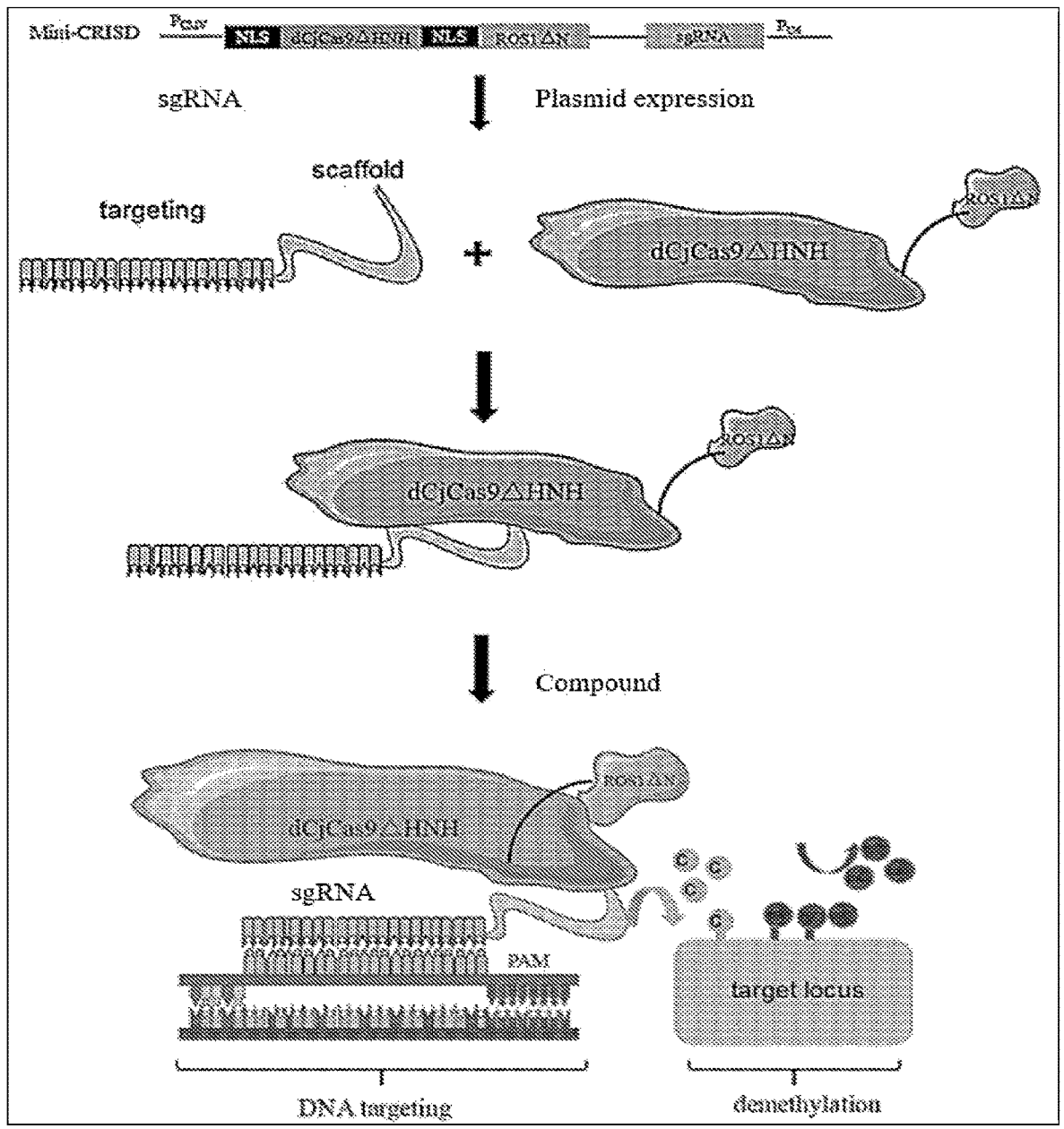
FIG. 1 illustrates a schematic flowchart of a targeted DNA demethylation method of the disclosure.

In order to facilitate the understanding of the disclosure, a more comprehensive description of the disclosure will be given below. The disclosure can be implemented in many different forms and is not limited to embodiments described herein. On the contrary, the purpose of providing the embodiments is to make a more thorough and comprehensive understanding of the disclosure.

Experimental procedures in which specific conditions are not indicated in the following examples are generally performed under conventional conditions, such as those described in Sambrook et al., Molecular Cloning: Laboratory Manual (New York: Cold Spring Harbor Laboratory Press, 1989), or as recommended by manufacturers. Various common chemical reagents used in the embodiments are commercially available products.

Unless otherwise defined, all technical and scientific terms used in the disclosure have the same meanings as those commonly understood by those skilled in the related art of the disclosure. The terms used in the specification of the disclosure are only for the purpose of describing specific embodiments, and are not used to limit the disclosure. The term "and/or" as used in the disclosure includes any and all combinations of one or more related listed items.

Some embodiments of the disclosure relate to a fusion protein, which includes a truncated nuclease inactivated *Campylobacter jejuni* clustered regularly interspaced short palindromic repeat associated endonuclease 9 abbreviated as CjCas9 (also referred to as dCjCas9ΔHNH) and a truncated repressor of silencing 1 abbreviated as ROS1 (also referred to as ROS1ΔN) connected by an intermediate sequence including a flexible linker. The truncated CjCas9 (dCjCas9ΔHNH) is an amino acid fragment obtained by removing amino acids at positions 481-640 of a CjCas9 protein, connecting remaining amino acids with a flexible linker, and performing D8A point mutation (the 8$^{th}$ amino acid is mutated from D to A). The truncated ROS1 (ROS1ΔN) is an amino acid fragment obtained by removing amino acids at positions 1-509 and 628-855 of a ROS1 protein and connecting remaining amino acids with a flexible linker, and an amino acid at position 971 of the ROS1 protein is aspartic acid (Asp).

In some embodiments, an amino acid composition of the truncated CjCas9 from the N-terminal to the C-terminal is a sequence shown in SEQ ID NO: 1 or a sequence with one or more amino acid mutations, substitutions but unchanged biological activity, a flexible linker, and a sequence shown in SEQ ID NO: 2 or a sequence with one or more amino acid mutations, substitutions but unchanged biological activity sequentially connected in that order.

In some embodiments, an amino acid composition of the truncated ROS1 from an N-terminal to a C-terminal is a sequence shown in SEQ ID NO: 3 or a sequence with one or more amino acid mutations, substitutions but unchanged biological activity, the flexible linker, and a sequence shown in SEQ ID NO: 4 or a sequence with one or more amino acid mutations, substitutions but unchanged biological activity sequentially connected in that order.

The fusion protein of the disclosure is fused according to the sequence of CjCas9ΔHNH-ROS1ΔN, i.e., the C-terminal of CjCas9ΔHNH is fused with the N-terminal of ROS1ΔN. Alternatively, the fusion protein can also be fused with the sequence of ROS1ΔN-CjCas9ΔHNH, i.e., the N-terminal of CjCas9ΔNHNH is fused with the C-terminal of ROS1ΔN.

In some embodiments, the fusion protein (CjCas9ΔHNH-ROS1ΔN) from an N-terminal to a C-terminal sequentially includes:

a sequence shown in SEQ ID NO: 1 or a sequence with one or more amino acid mutations, substitutions but unchanged biological activity, a flexible linker, and a sequence shown in SEQ ID NO: 2 or a sequence with one or more amino acid mutations, substitutions but unchanged biological activity;
an intermediate sequence; and
a sequence shown in SEQ ID NO: 3 or a sequence with one or more amino acid mutations, substitutions but unchanged biological activity, a flexible linker, and a sequence shown in SEQ ID NO: 4 with one or more amino acid mutations, substitutions but unchanged biological activity.

In some embodiments, the truncated CjCas9 and truncated ROS1 are connected by the intermediate sequence. The intermediate sequence mainly includes a nuclear localization signal (NLS) peptide, a flexible linker, and restriction enzyme cutting sites (also referred to as enzyme digestion sites) used in molecular cloning.

In some embodiments of the disclosure, the intermediate sequence is as shown in SPKKKRVEASK-LGGGGGGGGSGSVD shown in SEQ ID NO: 23.

In some embodiments, a front end of the truncated CjCas9 of the fusion protein includes a preamble sequence including an NLS peptide and restriction enzyme cutting sites. For example, the preamble sequence is SPKKKRVEAS shown in SEQ ID NO: 24.

The linker is a linker sequence used for connecting polypeptides, can connect two polypeptides and naturally fold the two polypeptides into a desired structure, and is generally a short peptide with hydrophobicity and certain stretchability. The purpose of the disclosure is to separate the two fused amino acid sequences, so as to alleviate their mutual interference, and maintain their respective activity and function. Such peptide linkers include, but are not limited to, for example, various soft linkers (also referred to as flexible linkers) consisting of the following amino acids: GGGGSGGGGSGGGGS shown in SEQ ID NO: 25, GSSGN shown in SEQ ID NO: 26, GGGSGG shown in SEQ ID NO: 27.

Nuclear localization signals (NLS) provide for nuclear transport of the protein to which the NLS is connected. For example, in the disclosure, dCjCas9ΔHNH and ROS1ΔN will enter the nucleus after connecting with NLS, improving the efficiency of DNA demethylation in the nucleus. Such nuclear positioning signals include, but are not limited to, SPKKKRVEAS shown in SEQ ID NO: 24 and GPKKKRKV shown in SEQ ID NO: 28. In order to detect the expression of fusion protein in protein expression and localization research, a tag sequence can be added to the fusion protein. In some embodiments of the disclosure, DYKDDDDK shown in SEQ ID NO: 29 (FLAG tag) is added to the preamble sequence.

In other embodiments of the disclosure, a nucleotide sequence encoding the fusion protein or a nucleotide sequence encoding the same amino acids with one or more nucleotide mutations is provided. For example, the above nucleotide sequences encode the same amino acid sequence due to codon optimization or codon degeneracy.

In other embodiments of the disclosure, an expression vector (Mini-CRISD plasmid) capable of expressing the fusion protein is provided.

The vectors can be plasmids, viruses (such as adenovirus vectors, retroviruses or lentiviruses, or adeno-associated virus vectors) or other expression vectors known in the art.

In some embodiments, the vector includes a DNA sequence for expressing single guide RNA (sgRNA), and each the sgRNA sequence includes a skeleton sequence that binds to CjCas9ΔHNH (truncated CjCas9) and a recognition sequence for recognizing a target DNA.

The nucleotides contained in the recognition sequence are correspondingly changed for different DNA targets and are completely complementary to the DNA target sequence. A length of the recognition sequence is usually preferably 20, 21, or 22 nucleotides, but the length of the recognition sequence can be in a range of from 10 to 35 nucleotides.

The skeleton sequence is a fixed 73 nucleotide fragment as shown in SEQ ID NO: 21. Accordingly, the DNA sequence for expressing the skeleton sequence of sgRNA on the vector is shown in SEQ ID NO: 22.

In other embodiments of the disclosure, a kit for targeted DNA demethylation is provided, which includes an expression vector capable of expressing the above fusion protein or includes the above fusion protein.

In some embodiments, the kit further includes sgRNA sequences, and each of the sgRNA sequences includes a skeleton sequence capable of combining with the truncated CjCas9 and a recognition sequence capable of recognizing a target DNA.

The sgRNA sequence is expressed and obtained in the expression vector, that is, the expression vector includes a DNA sequence for expressing sgRNA.

The sgRNA sequence can also be expressed in another expression vector independently, without being expressed in the same vector expressing fusion protein, that is, the kit further includes an expression vector with a DNA sequence capable of expressing sgRNA.

In other embodiments of the disclosure, a targeted DNA demethylation method is provided, which includes the following steps:
step S1, constructing an expression vector expressing the fusion protein;
step S2, obtaining a sgRNA sequence, where the sgRNA sequence includes a skeleton sequence capable of combining with the CjCas9ΔHNH (truncated CjCas9) and a recognition sequence completely complementary to a target sequence on the target DNA; and
step S3, introducing the expression vector and the sgRNA sequence into a target containing target DNA, and performing targeted demethylation.

In the above step S2, the obtaining a sgRNA sequence includes inserting the DNA sequence expressing the sgRNA into the expression vector expressing the fusion protein, or inserting the DNA sequence expressing the sgRNA into another separate vector, or obtaining the sgRNA sequence by synthesis.

In other embodiments of the disclosure, an application of the above fusion protein or the expression vector in inducing targeted DNA demethylation in vivo and/or ex vivo and/or in vitro is provided.

Specifically, in vivo and/or ex vivo represents that the expression vector or the fusion protein are delivered into vivo and/or ex vivo using viral vectors (e.g., adeno-associated viruses, lentiviruses) or non-viral vectors (e.g., liposomes, nanomaterials).

In vitro represents that the expression vector or the fusion protein are delivered into cells using viral vectors (e.g., adeno-associated viruses, lentiviruses) or non-viral vectors (e.g., liposomes, nanomaterials) or other delivery methods (such as electroporation, microinjection).

In other embodiments of the disclosure, an application of the above fusion protein or the expression vector in preparing a medicine of drugs for cancer treatment based on targeted DNA demethylation is provided.

In other embodiments of the disclosure, an application of the above fusion protein or the expression vector in preparing a medicine for treatment of diseases caused by abnormal DNA methylation is provided.

The diseases caused by abnormal DNA methylation include tumors, cancers, or metabolic diseases and other related diseases.

In some embodiments of the disclosure, a fusion control protein is provided, which includes a truncated CjCas9 (dCjCas9ΔHNH) and a truncated ROS1 (ROS1ΔN) connected by an intermediate sequence including a flexible linker. The truncated CjCas9 is an amino acid fragment obtained by removing amino acids at positions 481-640 of a CjCas9 protein, connecting remaining amino acids with a flexible linker, and performing D8A point mutation (the $8^{th}$ amino acid is mutated from D to A). The truncated ROS1 (ROS1ΔN) is an amino acid fragment obtained by removing amino acids at positions 1-509 and 628-855 of a ROS1 protein and connecting remaining amino acids with a flexible linker, and an amino acid at position 971 of the ROS1 protein is not aspartic acid (Asp).

The fusion control protein can be used for experimental control. The amino acid at 971 position of the ROS1 protein is not aspartic acid (Asp), for example, the aspartic acid is mutated into asparagine (Asn).

The disclosure is further described in the following specific embodiments, but is not intended to limit the protection scope of the disclosure.

Embodiment 1

In order to achieve Mini-CRISD, CjCas9 and ROS1 proteins are engineered and truncated, respectively, and fused to express on this basis. Mini-CRISD greatly reduces the size of the fusion protein (i.e., the size of an inserted sequence on the expression vector) while retaining the targeting of Cas9 and the demethylation function of ROS1, facilitating gene delivery in vivo and in vitro, while retaining the corresponding biological activity. Mini-CRISD is first established based on two confirmed findings: (1) after removing the HNH domain of amino acids at positions 481-640 of CjCas9 (referred to as CjCas9ΔHNH), RuvC domain retains the single-strand cleavage function in vitro experiments (Yamada M, Watanabe Y, Gootenberg J S, et al., "Crystal Structure of the Minimal Cas9 from *Campylobacter jejuni* Reveals the Molecular Diversity in the CRISPR-Cas9 Systems", Mol Cell, 2017, 65 (6): 1109-1121); (2) after removing amino acids at positions 1-509 and 628-855 at the N-terminal of the of ROS1 purified in vitro, the remaining amino acid sequence (referred to as ROS1ΔN) retains the demethylation ability in vitro experiments (Hong S, Hashimoto H, Kow Y W, et al., "The carbon-terminal domain of ROS1 is essential for 5-methylcytosine DNA glycolytic activity", J Mol Biol, 2014 426 (22): 3703-3712). On this basis, the CjCas9 endonuclease activity is completely inactivated by D8A point mutation and only its ability to target DNA is retained (referred to as dCjCas9ΔHNH). In this situation, it is confirmed ROS1ΔN also has demethylase activity in vivo. By performing fusion expression of dCjCas9ΔHNH and ROS1ΔN together with the corresponding sgRNA, the fusion expression protein has targeted DNA demethylation ability in vivo. In addition, the creative use of the truncated dCjCas9ΔHNH and the truncated ROS1ΔN proteins greatly reduces the size of the fusion protein and the insertion sequence on the expression vector, thereby enabling gene delivery in vivo and in vitro while retaining the corresponding biological activity.

Compared with the prior art, the advantages of the Mini-CRISD of the disclosure mainly include three aspects, genetic regulation, molecular technology, and gene targeting. (1), regarding to the advantages of genetic regulation, ROS1 glucosidase from plants does not produce 5 mC derivatives in the process of demethylation, which avoids the problem of generating 5 mC derivatives and introducing additional genetic signals in the current method of using demethylation effectors from animals such as ten-eleven translocation 1 (TET1). (2), regarding to the advantages of molecular technology, Mini-CRISD has a brand-new sequence design, which has smaller genetic sequence and higher activity compared with the clustered regularly interspaced short palindromic repeat (CRISPR) system currently in use, Mini-CRISD has smaller gene sequences and higher activity, so that the expression vector has a smaller size, and the demethylation gene therapy based on viral delivery, which is difficult to achieve due to the size of the vector, is possible. (3) regarding to the advantage of gene targeting, based on CRISPR principle, Mini-CRISD has better targeting effect and lower miss rate compared with other targeting systems such as zinc finger proteins (ZNFs), transcription activator-like effectors (TALEs). The targeted DNA demethylation technology of the disclosure is the first time to use dCjCas9 as a DNA targeting tool, and also the first time to apply the truncated ROS1 to targeted DNA demethylation.

The targeted DNA demethylation method of the disclosure includes the following steps for construction (see FIG. 1).

Step 1, an expression plasmid vector (Mini-CRISD plasmid for short) expressing Mini-CRISD complex (fusion expression protein of dCjCas9ΔHNH and ROS1ΔN and sgRNA) is constructed. The plasmid contains the following key elements to achieve targeted DNA demethylation. (1) A DNA sequence that can express dCjCas9ΔHNH, and dCjCas9ΔHNH refers to that CjCas9 protein removes its HNH domain (amino acids at positions 481-640), the remaining amino acids are connected by a flexible linker (such as GGGSGG shown in SEQ ID NO: 27), and D8A point mutation is performed. (2) A DNA sequence that can express ROS1ΔN, ROS1ΔN refers to that ROS1 protein removes its amino acids at positions 1-509 and 628-855, and the remaining amino acids are connected by a flexible linker (such as GSSGN shown in SEQ ID NO: 26). (3) A DNA sequence used to express one or more sgRNAs. Each sgRNA sequence includes two parts, one part is a fixed skeleton sequence (also referred to as a scaffold) binding to CjCas9ΔHNH, the other part is a recognition sequence (also referred to as targeting) that changes according to different DNA targets, and the other part can be replaced by a blank sequence (also referred to as a spacer). The blank sequence contains restriction enzyme cutting sites (such as BsmbI, BbsI, etc.), which facilitates the replacement of the blank sequence with a recognition sequence. In addition to the above three key elements, the plasmid further contains the following four auxiliary elements to achieve Mini-CRISD. (4) NLS peptides introduced at both ends of dCjCas9ΔHNH, which is used to introduce the fusion-expressed protein into the nucleus. (5) A flexible linker (such as GGGGGGSGGGGGGGGGGGGG shown in SEQ ID NO: 30) connected between dCjCas9ΔHNH and ROS1ΔN. (6) Promoters that drive the expression of a sequence of dCjCas9ΔHNH-ROS1ΔN, such as CMV promoter, EF1α promoter, etc. (7) Promoters that drive the transcription of sgRNA sequences, such as U6 promoter, H1 promoter, etc.

In addition, the target DNA sequence should contain the protospacer adjacent motif (PAM) sequence required by CjCas9, that is, the 3' end of the target sequence should be immediately adjacent to 5'-ACA-3', 5'-NNNNNRYAC-3' or 5'-NNNVRYAC-3' (where N represents any base of A/T/C/G, V represents any base of A/G/C, R represents any base of A/G, and Y represents any base of T/C). The corresponding recognition sequence is designed according to the DNA target sequence and the blank sequence on the Mini-CRISD plasmid is replaced to obtain the Mini-CRISD plasmid (carrying sgRNA targeting specific DNA) for specific DNA target.

Step 2, Mini-CRISD plasmid is introduced into cells containing target DNA. For in vitro/ex vitro experiments, the constructed vector is introduced into the cells through liposome transfection, electroporation and any other effective delivery methods. For in vivo experiments, all the constructed vector or part of the constructed vector containing functional fragments thereof, or the key elements of Mini-CRISD, are introduced into the body through any effective introduction method such as virus infection, liposome encapsulation, etc. After the dCjCas9ΔHNH-ROS1ΔN fusion protein and sgRNA are assembled into a complex, they will target specific DNA sequences and realize demethylation.

It should be emphasized that Mini-CRISD is also applicable to the case where a single vector is not used, i.e., dCjCas9ΔHNH-ROS1ΔN fusion protein and sgRNA do not have to be constructed on the same vector as described in step 1. For example, the fusion protein and sgRNA can be co-expressed using different vectors, expressed separately and then mixed together to form a complex, or sgRNA can be obtained by chemical synthesis. The targeted DNA demethylation provided by the disclosure can be performed as long as dCjCas9ΔHNH-ROS1ΔN fusion protein and sgRNA are obtained by appropriate means.

When the target DNA is demethylated, the CjCas9ΔHNH of the fusion protein is combined with the skeleton sequence of sgRNA to form a complex between the fusion protein and sgRNA. The complex then binds to the target sequence of the target DNA through the recognition sequence of sgRNA, and the demethylation of target DNA is realized through the demethylase activity of the ROS1ΔN of the fusion protein.

TABLE 1

Amino acid sequences of the disclosure

| | |
|---|---|
| The amino acid sequence of CjCas9, corresponding to the most original CjCas9. Specifically, the part of dCjCas9ΔHNH in the sequence of the fusion protein to be protected is obtained by removing amino acids at positions 481-640 of a CjCas9 protein, connecting remaining amino acids with a flexible linker, and performing D8A point mutation. | MARILAFDIGISSIGWAFSENDELKDCGVRIFTKVENP KTGESLALPRRLARSARKRLARRKARLNHLKHLIAN EFKLNYEDYQSFDESLAKAYKGSLISPYELRFRALNE LLSKQDFARVILHIAKRRGYDDIKNSDDKEKGAILKA IKQNEEKLANYQSVGEYLYKEYFQKFKENSKEFTNV RNKKESYERCIAQSFLKDELKLIFKKQREFGFSFSKK FEEEVLSVAFYKRALKDFSHLVGNCSFFTDEKRAPK NSPLAFMFVALTRIINLLNNLKNTEGILYTKDDLNAL LNEVLKNGTLTYKQTKKLLGLSDDYEFKGEKGTYFI EFKKYKEFIKALGEHNLSQDDLNEIAKDITLIKDEIKL KKALAKYDLNQNQIDSLSKLEFKDHLNISFKALKLV TPLMLEGKKYDEACNELNLKVAINEDKKDFLPAFNE TYYKDEVTNPVVLRAIKEYRKVLNALLKKYGKVHK INIELAREVGKNHSQRAKIEKEQNENYKAKKDAELE CEKLGLKINSKNILKLRLFKEQKEFCAYSGEKIKISDL QDEKMLEIDHIYPYSRSFDDSYMNKVLVFTKQNQEK LNQTPFEAFGNDSAKWQKIEVLAKNLPTKKQKRILD KNYKDKEQKNFKDRNLNDTRYIARLVLNYTKDYLD FLPLSDDENTKLNDTQKGSKVHVEAKSGMLTSALR HTWGFSAKDRNNHLHHAIDAVIIAYANNSIVKAFSDF KKEQESNSAELYAKKISELDYKNKRKFFEPFSGFRQK VLDKIDEIFVSKPERKKPSGALHEETFRKEEEFYQSY GGKEGVLKALELGKIRKVNGKIVKNGDMFRVDIFK HKKTNKFYAVPIYTMDFALKVLPNKAVARSKKGEIK DWILMDENYEFCFSLYKDSLILIQTKDMQEPEFVYY NAFTSSTVSLIVSKHDNKFETLSKNQKILFKNANEKE VIAKSIGIQNLKVFEKYIVSALGEVTKAEFRQREDFK K (SEQ ID NO: 7) |
| The amino acid sequence of dCjCas9ΔHNH Note: the bold and underlined site (i.e., A) is the critical D8A mutation-inactivating site that renders dCjCas9ΔHNH incapable of cleaving DNA; and italics sequence is an alternative flexible linker. | MARILAFAIGISSIGWAFSENDELKDCGVRIFTKVENP KTGESLALPRRLARSARKRLARRKARLNHLKHLIAN EFKLNYEDYQSFDESLAKAYKGSLISPYELRFRALNE LLSKQDFARVILHIAKRRGYDDIKNSDDKEKGAILKA IKQNEEKLANYQSVGEYLYKEYFQKFKENSKEFTNV RNKKESYERCIAQSFLKDELKLIFKKQREFGFSFSKK FEEEVLSVAFYKRALKDFSHLVGNCSFFTDEKRAPK NSPLAFMFVALTRIINLLNNLKNTEGILYTKDDLNAL LNEVLKNGTLTYKQTKKLLGLSDDYEFKGEKGTYFI EFKKYKEFIKALGEHNLSQDDLNEIAKDITLIKDEIKL KKALAKYDLNQNQIDSLSKLEFKDHLNISFKALKLV TPLMLEGKKYDEACNELNLKVAINEDKKDFLPAFNE TYYKDEVTNPVVLRAIKEYRKVLNALLKKYGKVHK INIEL (SEQ ID NO: 1) *GGGSGG* (flexible linker shown in SEQ ID NO: 27) RYIARLVLNYTKDYLDFLPLSDDENTKLNDTQKGSK VHVEAKSGMLTSALRHTWGFSAKDRNNHLHHAIDA VIIAYANNSIVKAFSDFKKEQESNSAELYAKKISELDY KNKRKFFEPFSGFRQKVLDKIDEIFVSKPERKKPSGA LHEETFRKEEEFYQSYGGKEGVLKALELGKIRKVNG KIVKNGDMFRVDIFKHKKTNKFYAVPIYTMDFALKV LPNKAVARSKKGEIKDWILMDENYEFCFSLYKDSLIL |

TABLE 1-continued

Amino acid sequences of the disclosure

| | |
|---|---|
| | IQTKDMQEPEFVYYNAFTSSTVSLIVSKHDNKFETLS<br>KNQKILFKNANEKEVIAKSIGIQNLKVFEKYIVSALG<br>EVTKAEFRQREDFKK (SEQ ID NO: 2) |
| The amino acid sequence of ROS1, corresponding to the most original ROS1. Specifically, the part of ROS1ΔN in the sequence of the fusion protein to be protected is obtained by removing amino acids at positions 1-509 and 628-855 of a ROS1 protein and connecting remaining amino acids with a flexible linker. | MEKQRREESSFQQPPWIPQTPMKPFSPICPYTVEDQY<br>HSSQLEERRFVGNKDMSGLDHLSFGDLLALANTASL<br>IFSGQTPIPTRNTEVMQKGTEEVESLSSVSNNVAEQIL<br>KTPEKPKRKKHRPKVRREAKPKREPKPRAPRKSVVT<br>DGQESKTPKRKYVRKKVEVSKDQDATPVESSAAVET<br>STRPKRLCRRVLDFEAENGENQINGDIREAGEMESA<br>LQEKQLDSGNQELKDCLLSAPSTPKRKRSQGKRKG<br>VQPKKNGSNLEEVDISMAQAAKRRQGPTCCDMNLS<br>GIQYDEQCDYQKMHWLYSPNLQQGGMRYDAICSK<br>VFSGQQHNYVSAFHATCYSSTSQLSANRVLTVEERR<br>EGIFQGRQESELNVLSDKIDTPIKKKTTGHARFRNLS<br>SMNKLVEVPEHLTSGYCSKPQQNNKILVDTRVTVSK<br>KKPTKSEKSQTKQKNLLPNLCRFPPSFTGLSPDELWK<br>RRNSIETISELLRLLDINREHSETALVPYTMNSQIVLF<br>GGGAGAIVPVTPVKKPRPRPKVDLDDETDRVWKLL<br>LENINSEGVDGSDEQKAKWWEEERNVFRGRADSFI<br>ARMHLVQGDRRFTPWKGSVVDSVVGVFLTQNVSDH<br>LSSSAFMSLASQFPVPFVPSSNFDAGTSSMPSIQITYL<br>DSEETMSSPPDHNHSSVTLKNTQPDEEKDYVPSNET<br>SRSSSEIAISAHESVDKTTDSKEYVDSDRKGSSVEVD<br>KTDEKCRVLNLFPSEDSALTCQHSMVSDAPQNTERA<br>GSSSEIDLEGEYRTSFMKLLQGVQVSLEDSNQVSPN<br>MSPGDCSSEIKGFQSMKEPTKSSVDSSEPGCCSQQD<br>GDVLSCQKPTLKEKGKKVLKEEKKAFDWDCLRREA<br>QARAGIREKTRSTMDTVDWKAIRAADVKEVAETIKS<br>RGMNHKLAERIQGFLDRLVNDHGSIDLEWLRDVPPD<br>KAKEYLLSFNGLGLKSVECVRLLTLHHLAFPVDTNV<br>GRIAVRLGWVPLQPLPESLQLHLLEMYPMLESIQKY<br>LWPRLCKLDQKTLYELHYQMITFGKVFCTKSKPNCN<br>ACPMKGECRHFASAFASARLALPSTEKGMGTPDKNP<br>LPLHLPEPFQREQGSEVVQHSEPAKKVTCCEPIIEEPA<br>SPEPETAEVSIADIEEAFFEDPEEIPTIRLNMDAFTSNL<br>KKIMEHNKELQDGNMSSALVALTAETASLPMPKLKN<br>ISQLRTEHRVYELPDEHPLLAQLEKREPDDPCSYLLAI<br>WTPGETADSIQPSVSTCIFQANGMLCDEETCFSCNSI<br>KETRSQIVRGTILIPCRTAMRGSFPLNGTYFQVNEVF<br>ADHASSLNPINVPRELIWELPRRTVYFGTSVPTIFKGL<br>STEKIQACFWKGYVCVRGFDRKTRGPKPLIARLHFP<br>ASKLKGQQANLA (SEQ ID NO: 8) |
| The amino acid sequence of ROS1ΔN<br>Note: italics sequence is an alternative flexible linker, and the bold and underlined site (i.e., D) is the critical D971 active site, providing the demethylation ability. | GAGAIVPVTPVKKPRPRPKVDLDDETDRVWKLLLEN<br>INSEGVDGSDEQKAKWWEEERNVFRGRADSFIARM<br>HLVQGDRRFTPWKGSVVDSVVGVFLTQNVSDHLSSS<br>AFMSLASQFPV (SEQ ID NO: 3)<br>*GSSGN* (flexible linker shown in SEQ ID NO: 26)<br>AFDWDCLRREAQARAGIREKTRSTMDTVDWKAIRA<br>ADVKEVAETIKSRGMNHKLAERIQGFLDRLVNDHGS<br>IDLEWLRDVPPDKAKEYLLSFNGLGLKSVECVRLLT<br>LHHLAFPVDTNVGRIAVRLGWVPLQPLPESLQLHLL<br>EMYPMLESIQKYLWPRLCKLDQKTLYELHYQMITFG<br>KVFCTKSKPNCNACPMKGECRHFASAFASARLALPS<br>TEKGMGTPDKNPLPLHLPEPFQREQGSEVVQHSEPA<br>KKVTCCEPIIEEPASPEPETAEVSIADIEEAFFEDPEEIP<br>TIRLNMDAFTSNLKKIMEHNKELQDGNMSSALVALT<br>AETASLPMPKLKNISQLRTEHRVYELPDEHPLLAQLE<br>KREPDDPCSYLLAIWTPGETADSIQPSVSTCIFQANG<br>MLCDEETCFSCNSIKETRSQIVRGTILIPCRTAMRGSF<br>PLNGTYFQVNEVFADHASSLNPINVPRELIWELPRRT<br>VYFGTSVPTIFKGLSTEKIQACFWKGYVCVRGFDRK<br>TRGPKPLIARLHFPASKLKGQQANLA (SEQ ID NO: 4) |

TABLE 1-continued

Amino acid sequences of the disclosure

| | |
|---|---|
| The amino acid sequence of dCjCas9ΔHNH-ROS1ΔN, i.e., the sequence of the fusion protein to be protected Note: lowercase underlined sequence (i.e., dykddddk, also represented as DYKDDDDK shown in SEQ ID NO: 29) is a replaceable FLAG tag. Italics underlined sequences are NLS peptides (2 places in total). Italics sequences are replaceable flexible linkers (3 places in total). The bold and underlined sites are the critical D8A mutation-inactivating site (i.e., A) and the critical D971 active site (i.e., D). All the underlined amino acids are the amino acids formed by the transcription and translation of the enzyme cutting sites on the plasmid vector introduced for cloning and connecting the above fragments, and can be replaced by other amino acids (5 places in total). | Mdykddddk S PKKKRKV EAS (preamble sequence, also represented as SPKKKRKVEAS shown in SEQ ID NO: 24) MARILAFAIGISSIGWAFSENDELKDCGVRIFTKVENP KTGESLALPRRLARSARKRLARRKARLNHLKHLIAN EFKLNYEDYQSFDESLAKAYKGSLISPYELRFRALNE LLSKQDFARVILHIAKRRGYDDIKNSDDKEKGAILKA IKQNEEKLANYQSVGEYLYKEYFQKFKENSKEFTNV RNKKESYERCIAQSFLKDELKLIFKKQREFGFSFSKK FEEEVLSVAFYKRALKDFSHLVGNCSFFTDEKRAPK NSPLAFMFVALTRIINLLNNLKNTEGILYTKDDLNAL LNEVLKNGTLTYKQTKKLLGLSDDYEFKGEKGTYFI EFKKYKEFIKALGEHNLSQDDLNEIAKDITLIKDEIKL KKALAKYDLNQNQIDSLSKLEFKDHLNISFKALKLV TPLMLEGKKYDEACNELNLKVAINEDKKDFLPAFNE TYYKDEVTNPVVLRAIKEYRKVLNALLKKYGKVHK INIEL (SEQ ID NO: 1) GGGSGG (flexible linker shown in SEQ ID NO: 27) RYIARLVLNYTKDYLDFLPLSDDENTKLNDTQKGSK VHVEAKSGMLTSALRHTWGFSAKDRNNHLHHAIDA VIIAYANNSIVKAFSDFKKEQESNSAELYAKKISELDY KNKRKFFEPFSGFRQKVLDKIDEIFVSKPERKKPSGA LHEETFRKEEEFYQSYGGKEGVLKALELGKIRKVNG KIVKNGDMFRVDIFKHKKTNKFYAVPIYTMDFALKV LPNKAVARSKKGEIKDWILMDENYEFCFSLYKDSLIL IQTKDMQEPEFVYYNAFTSSTVSLIVSKHDNKFETLS KNQKILFKNANEKEVIAKSIGIQNLKVFEKYIVSALG EVTKAEFRQREDFKK (SEQ ID NO: 2) S PKKKRKV EASKL GGGGSGGGGSGGGGS VD (intermediate sequence, also represented as SPKKKRVEASKLGGGGGGGGSGSVD shown in SEQ ID NO: 23) GAGAIVPVTPVKKPRPRPKVDLDDETDRVWKLLLEN INSEGVDGSDEQKAKWWEEERNVFRGRADSFIARM HLVQGDRRFTPWKGSVVDSVVGVFLTQNVSDHLSSS AFMSLASQFPV (SEQ ID NO: 3) GSSGN (flexible linker shown in SEQ ID NO: 26) AFDWDCLRREAQARAGIREKTRSTMDTVDWKAIRA ADVKEVAETIKSRGMNHKLAERIQGFLDRLVNDHGS IDLEWLRDVPPDKAKEYLLSFNGLGLKSVECVRLLT LHHLAFPVDTNVGRIAVRLGWVPLQPLPESLQLHLL EMYPMLESIQKYLWPRLCKLDQKTLYELHYQMITFG KVFCTKSKPNCNACPMKGECRHFASAFASARLALPS TEKGMGTPDKNPLPLHLPEPFQREQGSEVVQHSEPA KKVTCCEPIIEEPASPEPETAEVSIADIEEAFFEDPEEIP TIRLNMDAFTSNLKKIMEHNKELQDGNMSSALVALT AETASLPMPKLKNISQLRTEHRVYELPDEHPLLAQLE KREPDDPCSYLLAIWTPGETADSIQPSVSTCIFQANG MLCDEETCFSCNSIKETRSQIVRGTILIPCRTAMRGSF PLNGTYFQVNEVFADHASSLNPINVPRELIWELPRRT VYFGTSVPTIFKGLSTEKIQACFWKGYVCVRGFDRK TRGPKPLIARLHFPASKLKGQQANLA (SEQ ID NO: 4) |
| The amino acid sequence of dCjCas9ΔHNH-ROS1ΔN-dead, i.e., negative control of the fusion protein sequence to be protected of the disclosure (inactivated version) Note: the underlined, bolded, and italicized amino acid (i.e., _N_) is inactivated by the critical D971 site mutation, which renders the fusion protein to be protected of the disclosure incapable of demethylation. All other parts are consistent with the fusion protein dCjCas9ΔHNH-ROS1ΔN. | ATMDYKDDDDKSPKKKRKVEASARILAFAIGISSIG WAFSENDELKDCGVRIFTKVENPKTGESLALPRRLA RSARKRLARRKARLNHLKHLIANEFKLNYEDYQSFD ESLAKAYKGSLISPYELRFRALNELLSKQDFARVILHI AKRRGYDDIKNSDDKEKGAILKAIKQNEEKLANYQS VGEYLYKEYFQKFKENSKEFTNVRNKKESYERCIAQ SFLKDELKLIFKKQREFGFSFSKKFEEEVLSVAFYKR ALKDFSHLVGNCSFFTDEKRAPKNSPLAFMFVALTRI INLLNNLKNTEGILYTKDDLNALLNEVLKNGTLTYK QTKKLLGLSDDYEFKGEKGTYFIEFKKYKEFIKALG EHNLSQDDLNEIAKDITLIKDEIKLKKALAKYDLNQ NQIDSLSKLEFKDHLNISFKALKLVTPLMLEGKKYDE ACNELNLKVAINEDKKDFLPAFNETYYKDEVTNPVV LRAIKEYRKVLNALLKKYGKVHKINIELGGGSGGRY IARLVLNYTKDYLDFLPLSDDENTKLNDTQKGSKVH VEAKSGMLTSALRHTWGFSAKDRNNHLHHAIDAVII AYANNSIVKAFSDFKKEQESNSAELYAKKISELDYKN KRKFFEPFSGFRQKVLDKIDEIFVSKPERKKPSGALH EETFRKEEEFYQSYGGKEGVLKALELGKIRKVNGKI VKNGDMFRVDIFKHKKTNKFYAVPIYTMDFALKVLP NKAVARSKKGEIKDWILMDENYEFCFSLYKDSLILIQ TKDMQEPEFVYYNAFTSSTVSLIVSKHDNKFETLSK NQKILFKNANEKEVIAKSIGIQNLKVFEKYIVSALGE VTKAEFRQREDFKKSPKKKRKVEASKLGGGGSGGG GSGGGGSVDGAGAIVPVTPVKKPRPRPKVDLDDET |

TABLE 1-continued

Amino acid sequences of the disclosure

```
DRVWKLLLENINSEGVDGSDEQKAKWWEEERNVFR
GRADSFIARMHLVQGDRRFTPWKGSVVDSVVGVFL
TQNVSDHLSSSAFMSLASQFPVGSSGNAFDWDCLRR
EAQARAGIREKTRSTMDTVDWKAIRAADVKEVAETI
KSRGMNHKLAERIQGFLDRLVNDHGSIDLEWLRDVP
PDKAKEYLLSFNGLGLKSVECVRLLTLHHLAFPVNT
NVGRIAVRLGWVPLQPLPESLQLHLLEMYPMLESIQ
KYLWPRLCKLDQKTLYELHYQMITFGKVFCTKSKPN
CNACPMKGECRHFASAFASARLALPSTEKGMGTPD
KNPLPLHLPEPFQREQGSEVVQHSEPAKKVTCCEPIIE
EPASPEPETAEVSIADIEEAFFEDPEEIPTIRLNMDAFT
SNLKKIMEHNKELQDGNMSSALVALTAETASLPMPK
LKNISQLRTEHRVYELPDEHPLLAQLEKREPDDPCSY
LLAIWTPGETADSIQPSVSTCIFQANGMLCDEETCFS
CNSIKETRSQIVRGTILIPCRTAMRGSFPLNGTYFQVN
EVFADHASSLNPINVPRELIWELPRRTVYFGTSVPTIF
KGLSTEKIQACFWKGYVCVRGFDRKTRGPKPLIARL
HFPASKLKGQQANLA (SEQ ID NO: 5)
```

TABLE 2

Nucleotide sequence of the disclosure

The nucleotide sequence corresponds to that amino acids (fusion protein to be protected by the disclosure) use for expressing dCjCas9ΔHNH-ROS1ΔN on the plasmid vector.

```
atgGATTACAAGGACGACGATGACAAGtcgccgaagaaaaagc
gcaaggtcgaagcgtccATGGCTCGCATTCTGGCTTTTGCTAT
TGGAATCAGTAGCATTGGATGGGCCTTTTCTGAGAA
CGACGAGCTGAAGGATTGCGGGGTGAGAATTTTTAC
TAAGGTAGAGAACCCAAAGACCGGAGAGAGTCTCG
CCCTGCCCCGACGGCTGGCCAGGAGTGCTCGCAAA
AGGCTGGCCCGGCGCAAAGCCAGGCTGAACCATCT
CAAGCACCTTATCGCCAACGAGTTTAAGCTCAACTA
TGAAGATTACCAAAGTTTTGATGAGAGTCTGGCGAA
AGCCTATAAGGGTTCATTGATTTCACCCTATGAGCTG
CGCTTCCGCGCGCTGAATGAGTTGCTGAGTAAGCAA
GACTTCGCACGGGTTATCCTGCACATTGCAAAAAGG
CGCGGCTACGATGACATTAAGAACTCAGACGACAA
GGAGAAGGGGCCATCTTGAAGGCCATCAAACAGA
ATGAAGAGAAGCTCGCAAACTACCAGTCTGTGGGC
GAGTATCTTTACAAAGAGTACTTTCAGAAGTTCAAA
GAAAACAGTAAAGAATTTACTAACGTTCGGAATAAG
AAGGAGAGCTATGAGCGCTGCATTGCCCAGTCTTTC
CTGAAGGACGAACTCAAGCTGATTTTCAAGAAACA
GCGCGAATTTGGTTTCAGCTTTTCAAAAAAGTTCGA
AGAAGAGGTCCTGAGTGTGGCCTTTTACAAGCGGG
CTCTGAAAGACTTCAGTCATCTGGTTGGCAATTGCT
CATTTTTCACCGATGAAAAGCGCGCCCCTAAAAACT
CACCCCTCGCTTTATGTTCGTGGCCCTGACTAGGAT
CATAAATCTGCTGAACAACCTGAAAAATACCGAGGG
AATCCTCTACACTAAGGATGATCTTAACGCTCTGCTG
AACGAGGTTCTGAAGAATGGGACCCTGACCTATAAA
CAGACCAAGAAGCTCCTCGGGTTGAGCGATGATTAT
GAGTTTAAGGGCGAAAAGGGCACCTATTTTATTGAG
TTCAAAAAGTACAAGGAATTTATCAAAGCCCTGGGA
GAACACAATTTGAGTCAAGATGATCTGAATGAAATC
GCCAAAGACATTACTCTGATCAAGGACGAAATTAAG
CTGAAGAAGGCTTTGGCAAAATACGATCTGAATCAA
AATCAAATCGATTCACTGAGTAAACTGGAATTTAAA
GACCACCTTAATATAAGTTTCAAAGCGTTGAAACTG
GTGACCCCACTGATGCTCGAAGGTAAGAAATATGAC
GAAGCCTGCAACGAACTGAATCTGAAAGTGGCAAT
TAACGAAGATAAAAAGGACTTCTTGCCAGCCTTCAA
TGAGACTTATTACAAAGATGAAGTTACCAATCCGGT
CGTGTTGCGCGCTATCAAGGAGTATCGGAAGGTGCT
GAATGCCCTGCTGAAAAAATATGGGAAAGTGCACA
AAATCAACATTGAGCTTGGAGGTGGCAGTGGCGGGC
GGTACATAGCCAGACTCGTTTTGAACTATACAAAAG
ACTACCTGGACTTCCTGCCCCTGAGTGACGATGAAA
ACACCAAACTGAACGACACACAAAAAGGTAGCAA
GGTGCACGTAGAGGCCAAATCAGGTATGCTCACGA
GCGCCCTTCGCCATACATGGGGTTTTAGCGCTAAGG
ACCGCAACAATCATCTGCACCATGCCATTGACGCTG
TGATTATAGCCTACGCCAATAACTCTATCGTGAAGGC
ATTCAGCGACTTTAAGAAGGAGCAGGAGTCCAATTC
TGCCGAGTTGTACGCAAAAAAAATCTCAGAACTCG
ATTACAAGAACAAAAGAAAGTTCTTTGAGCCATTCA
```

TABLE 2-continued

Nucleotide sequence of the disclosure

GCGGATTTAGACAGAAAGTTTTGGACAAGATCGATG
AGATTTTCGTGTCTAAGCCCGAGAGAAAGAAGCCTT
CCGGCGCATTGCACGAAGAAACCTTCAGAAAAGAG
GAAGAGTTTTACCAGTCATATGGAGGCAAGGAGGG
CGTACTTAAGGCTCTGGAGCTTGGAAAGATTAGGAA
GGTCAATGGTAAAATTGTGAAGAATGGAGACATGTT
TAGGGTCGATATATTTAAGCACAAAAAGACCAATAA
ATTTTACGCCGTCCCAATCTATACGATGGACTTTGCA
CTGAAGGTCTTGCCCAACAAGGCAGTCGCTCGCAG
CAAAAAAGGGGAGATTAAGGATTGGATTCTGATGG
ATGAGAATTATGAGTTTTGCTTTAGCCTCTACAAGGA
TTCTCTGATCTTGATTCAAACAAAAGACATGCAGGA
GCCCGAGTTCGTGTACTACAACGCCTTCACTTCTAG
TACAGTGAGTCTGATCGTGTCTAAGCACGACAACAA
ATTCGAGACCCTCAGCAAGAACCAGAAGATCCTGTT
TAAGAACGCAAACGAGAAGGAAGTGATTGCAAAGA
GCATCGGCATACAGAATTTGAAAGTTTTTGAAAAAT
ACATTGTCTCCGCACTCGGCGAGGTTACCAAAGCCG
AGTTTCGGCAGAGGGAGGATTTCAAGAAA*agccccaag*
*aagaagagaaaggtgg*aggccagcAAGCTT*g-*
*gaggcggcggtagcgga*
*ggaggggtccggcggcggtagtg*tcgacGGCGCAGGTGCAA
TAGTACCTGTGACACCAGTTAAGAAACCCCGACCA
AGGCCTAAAGTGGACCTCGATGATGAAACGGATAG
AGTGTGGAAGCTCCTGCTGGAGAACATAAACTCTG
AAGGCGTCGATGGCAGCGACGAACAAAAGGCCAA
ATGGTGGGAGGAGGAACGAAACGTTTTTAGGGGAC
GAGCGGACTCATTCATCGCTCGCATGCACCTGGTGC
AAGGGGACAGGAGGTTTACTCCATGGAAGGGCTCC
GTAGTGGACTCAGTTGTGGGAGTGTTTTTGACCCAG
AACGTGAGCGACCACCTCAGTTCTTCAGCCTTCATG
TCTCTGGCTAGTCAATTCCCTGTT<u>*GGGTCCAGCGGCA*</u>
<u>*A*</u>CGCATTTGACTGGGACTGTCTTAGGCGCGAAGCCC
AGGCTAGGGCAGGTATTCGAGAAAAGACCCGCTCA
ACCATGGATACCGTGGATTGGAAAGCAATTAGAGCC
GCGGATGTTAAGGAGGTTGCAGAAACCATCAAGTC
CAGGGGAATGAATCACAAGCTCGCTGAAAGGATTC
AAGGGTTCCTTGACCGCCTCGTGAATGACCATGGCA
GTATCGATCTGGAATGGCTGAGGGACGTGCCCCCTG
ATAAAGCCAAAGAATACTTGCTTTCTTTCAATGGGTT
GGGGCTGAAATCCGTGGAGTGTGTACGGCTGTTGA
CACTCCACCACTTGGCATTCCCAGTGGACACAAAC
GTTGGAAGGATCGCTGTCAGACTCGGTTGGGTGCCT
CTGCAGCCTCTTCCAGAAAGCCTCCAACTTCACCTG
TTGGAGATGTATCCTATGCTGGAATCAATCCAGAAAT
ACCTGTGGCCACGCCTTTGCAAGCTGGACCAGAAA
ACACTGTATGAATTGCACTATCAGATGATCACCTTTG
GTAAAGTTTTCTGTACCAAGTCCAAGCCAAACTGTA
ATGCTTGTCCGATGAAAGGGGAGTGTCGCCATTTCG
CCTCTGCCTTTGCAAGCGCCAGACTGGCACTCCCAA
GCACCGAGAAGGGCATGGGAACTCCCGATAAAAAC
CCTTTGCCTCTGCACCTGCCTGAGCCCTTCCAAAGA
GAGCAGGGGAGCGAAGTGGTCCAGCATTCTGAACC
TGCCAAGAAAGTAACCTGTTGCGAACCAATCATTGA
AGAGCCTGCCAGTCCTGAACCAGAGACAGCAGAGG
TGAGCATCGCCGATATTGAGGAAGCCTTTTTCGAAG
ATCCCGAAGAGATCCCCACCATTCGGCTGAACATGG
ACGCCTTCACAAGTAACCTCAAGAAAATTATGGAAC
ATAACAAGGAACTCCAGGACGGGAATATGAGCAGT
GCCCTGGTGGCTCTGACAGCCGAAACAGCAAGTCT
GCCCATGCCTAAGTTGAAGAACATTTCACAGCTTCG
GACCGAGCATAGGGTTTATGAGCTGCCAGATGAGCA
CCCACTGCTGGCTCAGTTGGAGAAACGCGAACCAG
ACGATCCATGCAGTTACCTGCTGGCAATCTGGACAC
CGGGTGAGACAGCAGACAGCATTCAGCCATCAGTAT
CTACCTGCATATTTCAGGCAAATGGGATGTTGTGCG
ACGAGGAAACATGTTTTAGTTGCAATTCTATCAAGG
AGACCAGAAGTCAGATTGTGCGCGGCACTATTCTCA
TACCCTGTCGAACAGCAATGCGCGGTTCATTTCCAC
TCAACGGCACATACTTCCAGGTCAATGAAGTGTTTG
CCGATCATGCTTCCAGCCTGAATCCTATTAATGTTCC
ACGGGAATTGATATGGGAGCTTCCCCGACGCACCGT
CTATTTTGGTACATCCGTCCCTACCATCTTCAAAGGA
CTCTCAACCGAGAAGATTCAAGCCTGTTTTTGGAAG TABLE 2-continued Nucleotide sequence of the disclosure GGGTACGTTTGCGTGAGAGGATTTGACAGAAAGAC
TAGGGGGCCTAAACCTCTTATAGCCCGCCTGCACTT
TCCTGCCTCTAAGCTGAAGGGCCAACAAGCTAACTT
GGCC (SEQ ID NO: 6)

Figure 2:
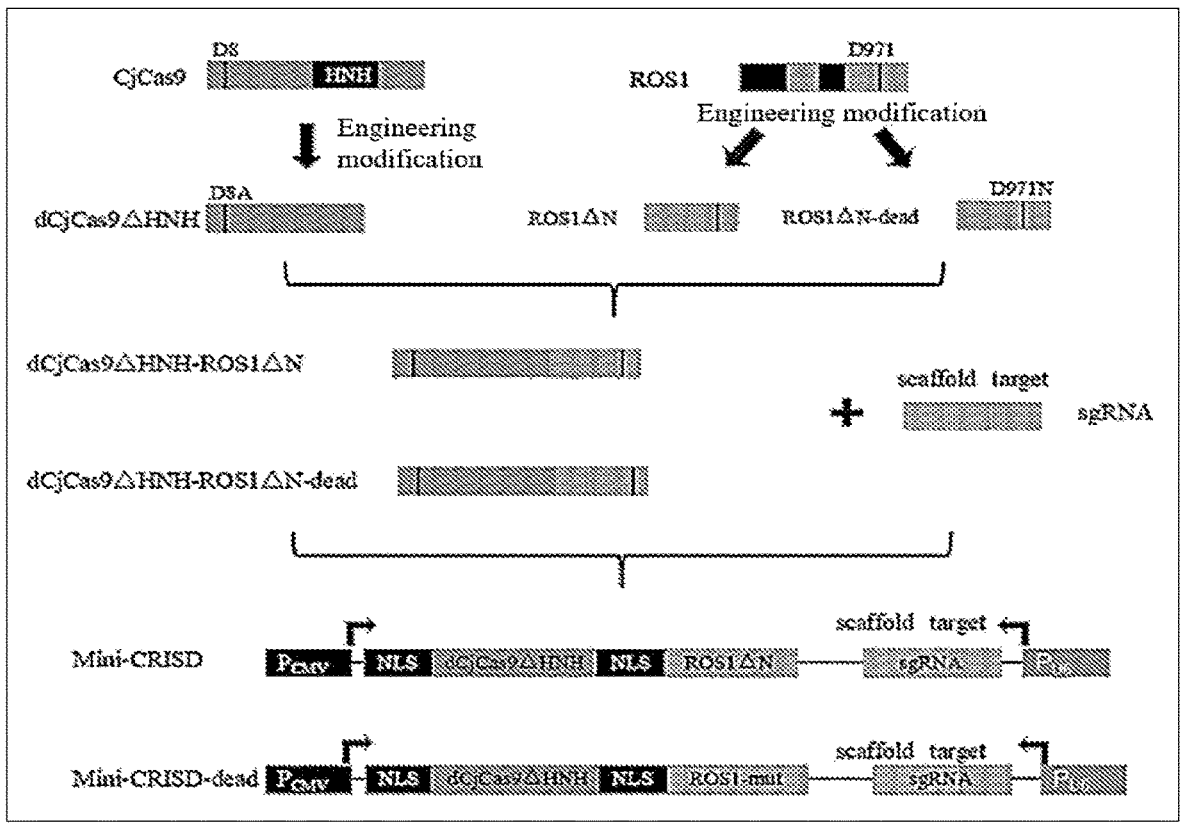
FIG. 2 illustrates a schematic diagram of a construction process of a miniature CjCas9-ROS1 induced specific demethylation (Mini-CRISD) plasmid vector.

Construction of Mini-CRISD plasmid vector and construction of Mini-CRISD-dead (mutation of D971N active site, dead means loss of demethylation ability) control plasmid (see Table 1 for specific sequences). The design idea of the plasmid vector is shown in FIG. 2.

Figure 3:
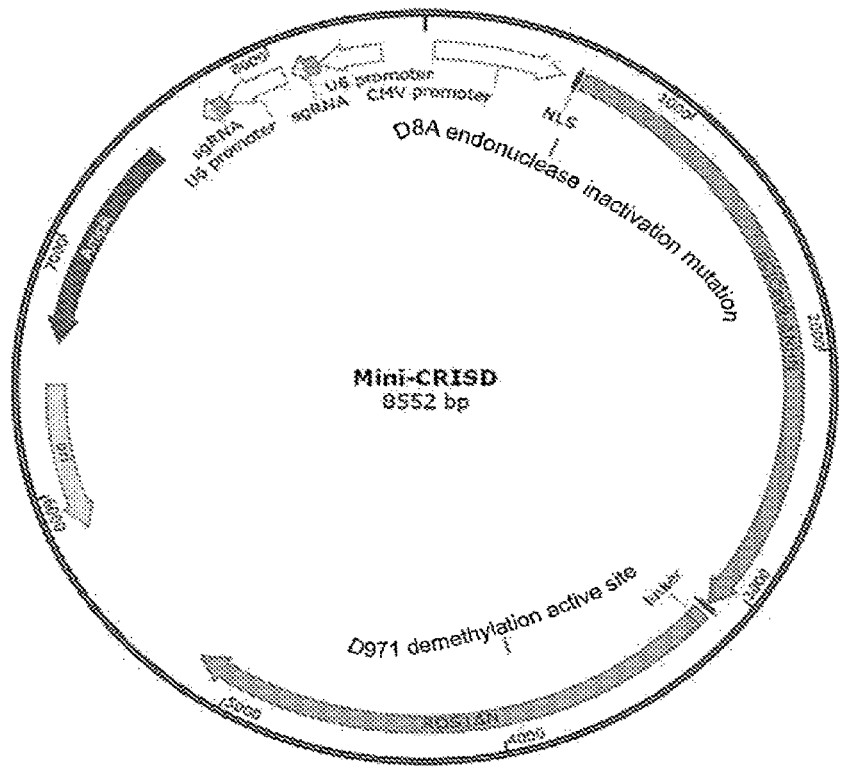
FIG. 3 illustrates a schematic diagram of the Mini-CRISD plasmid vector.

The detailed steps of plasmid construction of the disclosure are as follows:

1. A plasmid vector (as shown in FIG. 3) containing the key and auxiliary elements of Mini-CRISD described in step 1 of the above technical solution is constructed by means of whole gene synthesis, which is completed by Nanjing Tsingke Biotechnology Co., Ltd.

The design of the plasmid vector includes: (1) removing the HNH domain (amino acids at positions 481-640) of CjCas9 and performing D8A point mutation, so that CjCas9 loses its endonuclease activity and only retains the ability to target DNA (referred to as dCjCas9ΔHNH); (2) removing amino acids at positions 1-509 and 628-855 of ROS1 protein, and retaining the demethylation activity of the remaining amino acid sequence (referred to as ROS1ΔN); (3) taking dCjCas9ΔHNH and ROS1ΔN be expressed as a fusion protein (dCjCas9ΔHNH-ROS1ΔN) through a flexible linker; (4) two expression elements of sgRNA, each sgRNA sequence includes a fixed skeleton sequence (also referred to as scaffold) and a blank sequence (also referred to as spacer) that can be removed by BsmbI or BbsI digestion.

The nucleotides of the skeleton sequence (also referred to as scaffold) are as follows: guuuuagucccugaaaagg-gaaaaaaaaagaguugcggacugcgggguuaaucccuaaaccgc (SEQ ID NO: 21).

Accordingly, the DNA sequence that expresses the skeleton sequence of sgRNA is gttttagtcctgaaaaggga-taaaaaaaagagtttgcggcactctctctaaaccgc (SEQ ID NO: 22)

When the blank sequence on the plasmid vector is replaced by the recognition sequence (also referred to as targeting) for specific DNA target by appropriate molecular cloning means, the Mini-CRISD expression plasmid carrying sgRNA targeting specific DNA is obtained.

It should be emphasized that Mini-CRISD is also applicable to the case where the above plasmid vector is not used, that is, the dCjCas9ΔHNH-ROS1ΔN fusion protein and sgRNA do not have to be constructed on the same plasmid as described in step 1. For example, the fusion protein and sgRNA can be co-expressed using different plasmids, or expressed in the form of other non-plasmids such as mRNA, or other expression vectors known in the art such as virus vectors. For another example, the fusion protein can be obtained by in vitro expression and purification, and mixed with the sgRNA obtained by chemical synthesis to form a complex. The targeted DNA demethylation provided by the disclosure can be performed as long as dCjCas9ΔHNH-ROS1ΔN fusion protein and sgRNA are obtained by appropriate means. Therefore, Mini-CRISD is not limited to the specific plasmid described in this embodiment.

2. The Mini-CRISD-dead control plasmid is constructed, which loses the demethylation ability of ROS1 by introducing D971N amino acid point mutation, as the control of Mini-CRISD in other embodiments below. The specific construction method is as follows.

The Mini-CRISD plasmid is used as a template for point mutation. The QuickMutation™ Site-Directed Mutagenesis Kit (article No. D0206, purchased from Beyotime Biotechnology Co., Ltd) is used, and two complementary primers are designed according to the experimental requirements (see the following table for primer sequences).

ROS1-dead-D971N-F  TTGGCATTCCCAGTGAACACAAACGTTGGAAG
                   (SEQ ID NO: 9)

ROS1-dead-D971N-R  CTTCCAACGTTTGTGTTCACTGGGAATGCCAA
                   (SEQ ID NO: 10)

The point mutation PCR reaction system is as follows:

| Reagent | Final concentration | Volume |
| --- | --- | --- |
| 10× BeyoFusion Buffer | 1× | 5 μL |
| Primer mixture (10 μM) | 0.4 μM | 2 μL |
| dNTP mix (2.5 mM) | 0.25 mM | 5 μL |
| Mini-CRISD plasmid | 200 ng | 1 μL |
| BeyoFusion™ DNA Polymerase | 1/50 | 1 μL |
| Total volume after addition of nuclease-free water | — | 50 μL |

The reaction conditions of PCR are as follows:

| Procedures | Cycle number | Temperature | Time |
| --- | --- | --- | --- |
| 1 | 1 | 95° C. | 3 minutes |
| 2 | 20 | 95° C. | 30 seconds |
|   |   | 55° C. | 30 seconds |
|   |   | 68° C. | 60 seconds per kilobases (sec/kb) |
| 3 | 1 | 68° C. | 15 minutes |
| 4 | 1 | 4° C. | Keeping for a long time |

After PCR reaction, 1 μL DpnI restriction enzyme is directly added into the PCR reaction system, mixed evenly and incubated at 37° C. for 5 minutes. After DpnI digestion, 5-10 μL of products after DpnI digestion are added into every 100 μL of competent bacteria (TSINGKE Trelief® 5α Chemically Competent Cell, Article No. TSC-001) for transformation. For the obtained transformed clones, 3-5 clones are selected and sent for sequencing, and the sequencing results show that the expected point mutation is obtained.

Embodiment 2: Construction of Fluorescent Reporter Plasmids with Different Degrees of Methylation Using CpG methyltransferase M.SssI (NEB Inc, article No. M0226S) for different incubation time, different degrees of methylation of plasmid DNA can be achieved. The methylated plasmids are identified by HpaII restriction enzyme digestion. Since HpaII only cleaves unmethylated plasmid, the degree of methylation of plasmid can be evaluated according to HpaII cleavage (also referred to as HpaII digestion). The detailed steps are as follows.

1. The pEGFP-N1 fluorescent reporter plasmid (Clontech Laboratories Inc) is methylated in vitro, and different degrees of methylation could be obtained by CpG methyltransferase M.SssI for different incubation times of the plasmid. The in vitro methylation reaction system and conditions are as follows:

| Reagent | 50 uL reaction system |
| --- | --- |
| NEB Buffer ™ 2 (10×) | 5 uL |
| S-adenosylmethionine | 5 uL (Dilute to 1600 uM) |
| DNA | 1 ug |
| Methyltransferase M.SssI | 1 uL |
| Total volume after addition of nuclease-free water | 50 uL |

| Degree of methylation | Cycle number | Temperature | Reaction time | Instruction |
| --- | --- | --- | --- | --- |
| 50% | 1 | 37° C. | 30 minutes | |
|  | 1 | 65° C. | 20 minutes | |
| 75% | 1 | 37° C. | 45 minutes | |
|  | 1 | 65° C. | 20 minutes | |
| 100% | 2 | 37° C. | 2 hours | Two hours after the first cycle, 5 uL of S-adenosylmethionine and 1 uL of methyltransferase are added. |
|  | 1 | 65° C. | 20 min | |

Figure 4:
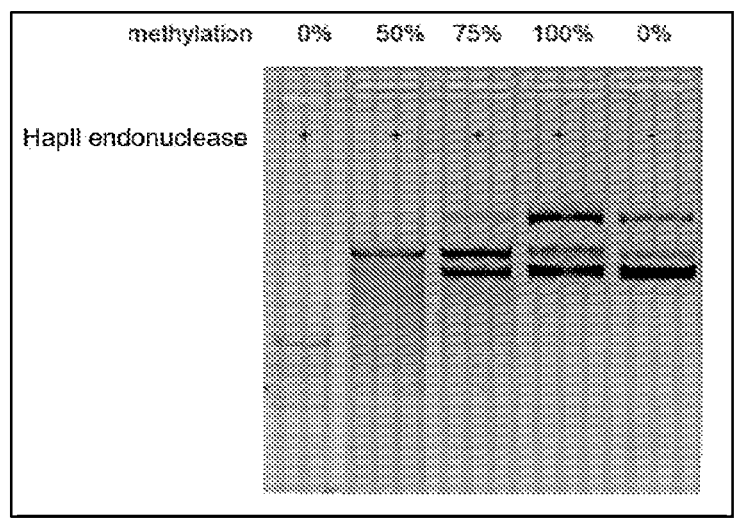
FIG. 4 illustrates a schematic diagram showing results of agarose gel electrophoresis after cleavage with HpaII restriction endonuclease.

2. The fluorescent reporter plasmid subjected to in vitro methylation reaction is subjected to HpaII restriction endonuclease cleavage. After agarose gel electrophoresis, the degree of methylation is determined based on the amount of DNA cleaved and non-cleaved by HpaII (FIG. 4).

Embodiment 3 Construction of Mini-CRISD Expression Plasmid Targeting CMV Promoter on pEGFP-N1 Fluorescent Reporter Plasmid 4 recognition sequences on CMV promoter that meet the requirements of CjCas9 PAM sequence are selected, as shown in the following table:

| | |
| --- | --- |
| $P_{CMV}$-SgRNA-3 | TCAAACCGCTATCCACGCCCAT (SEQ ID NO: 11) |
| $P_{CMV}$-SgRNA-4 | ATTGACGTCAATGGGAGTTTGT (SEQ ID NO: 12) |
| $P_{CMV}$-SgRNA-5 | CATTGACGCAAATGGGCGGTAG (SEQ ID NO: 13) |
| $P_{CMV}$-SgRNA-6 | CTCTGCTTATATAGACCTCCCA (SEQ ID NO: 14) |

1. The Mini-CRISD plasmid vector is subjected to BsmBI restriction endonuclease cleavage.
2. Carrier fragments are recovered by agarose gel electrophoresis.
3. Primers containing the above recognition sequences are synthesized. Each recognition sequence synthesizes two complementary primers, and the primer end contains sticky end sequence after BsmBI cleavage. The primers are annealed in the PCR instrument to form a double-stranded adaptor with BsmBI sticky end. Annealing method: 100 uM of each primer is dissolved in TE buffer, incubated at 95° C. for 5 minutes, and then slowly cooled to room temperature.
4. The annealed adapter fragment is reacted overnight with the Mini-CRISD plasmid vector recovered by enzyme digestion under the condition of T4 ligase 16° C.
5. The reacted product is transformed and monoclone is obtained. Sequencing shows that the expression plasmid is successfully constructed, that is, the blank sequence on the Mini-CRISD plasmid vector is replaced by the recognition sequence designed according to the CMV promoter, and four Mini-CRISD expression plasmids targeting the CMV promoter (carrying the sgRNA targeting the CMV promoter) are obtained.

Embodiment 4

Methylated fluorescent reporter plasmids are tested for demethylation using the mini-CRISD method in A549 cells. The detailed steps are as follows.

1) A549 cells are uniformly inoculated into 96-well plates with a density of 5000 cells/well and cultured in Ham's F-12K medium (containing 10% fetal bovine serum) in a constant temperature incubator at 37° C. and 5% $CO_2$.

2) After 24 hours, 50 ng each of the 50% methylated fluorescent reporter plasmid obtained in the embodiment 2 and the Mini-CRISD expression plasmid (carrying one of Pcmv-sgRNA-3, PcMv-sgRNA-4, PcMv-sgRNA-5 and Pcmv-sgRNA-6) obtained in the embodiment 3 are transfected into A549 cells simultaneously with lipofectamine 3000. The control group is simultaneously transfected with 50 ng of 50% methylated fluorescent reporter plasmid and 50 ng of Mini-CRISD (without sgRNA) plasmid vector.

3) After 48 hours, the culture medium is removed, rinsed twice with phosphate-buffered saline (PBS), and fixed with 4% paraformaldehyde. After 15 minutes, 4% paraformaldehyde is sucked out, and rinsed the PBS once. Then, 30 μL 4',6-Diamidino-2-Phenylindole (DAPI) staining solution is added into each well. After 5 minutes, the staining solution is sucked out, rinsed twice with PBS, and 100 μL PBS is added into each well.

4) Image acquisition and data processing are performed using the built-in software HCS Navigator Version 6.6.1 of the Thermo Fisher Scientific CellInsight™ CX7-LZR high content analysis platform. 25 fields of view are selected in each well of 96-well plate, and the images are taken at 405 nm and 488 nm excitation wavelengths in each field of view. After DAPI staining, the nucleus is blue at 405 nm excitation wavelength, and green fluorescent protein (GFP) expressed in cells is green at 488 nm excitation wavelength. The platform accurately locates the position of the nucleus by identifying the blue area, identifies the cell range with the fixed value of the expansion of the nucleus, calculates the green fluorescence value within each cell range, and finally calculates the average value of the green fluorescence intensity within the range of all marked cells in the 25 fields of view.

Figure 5:
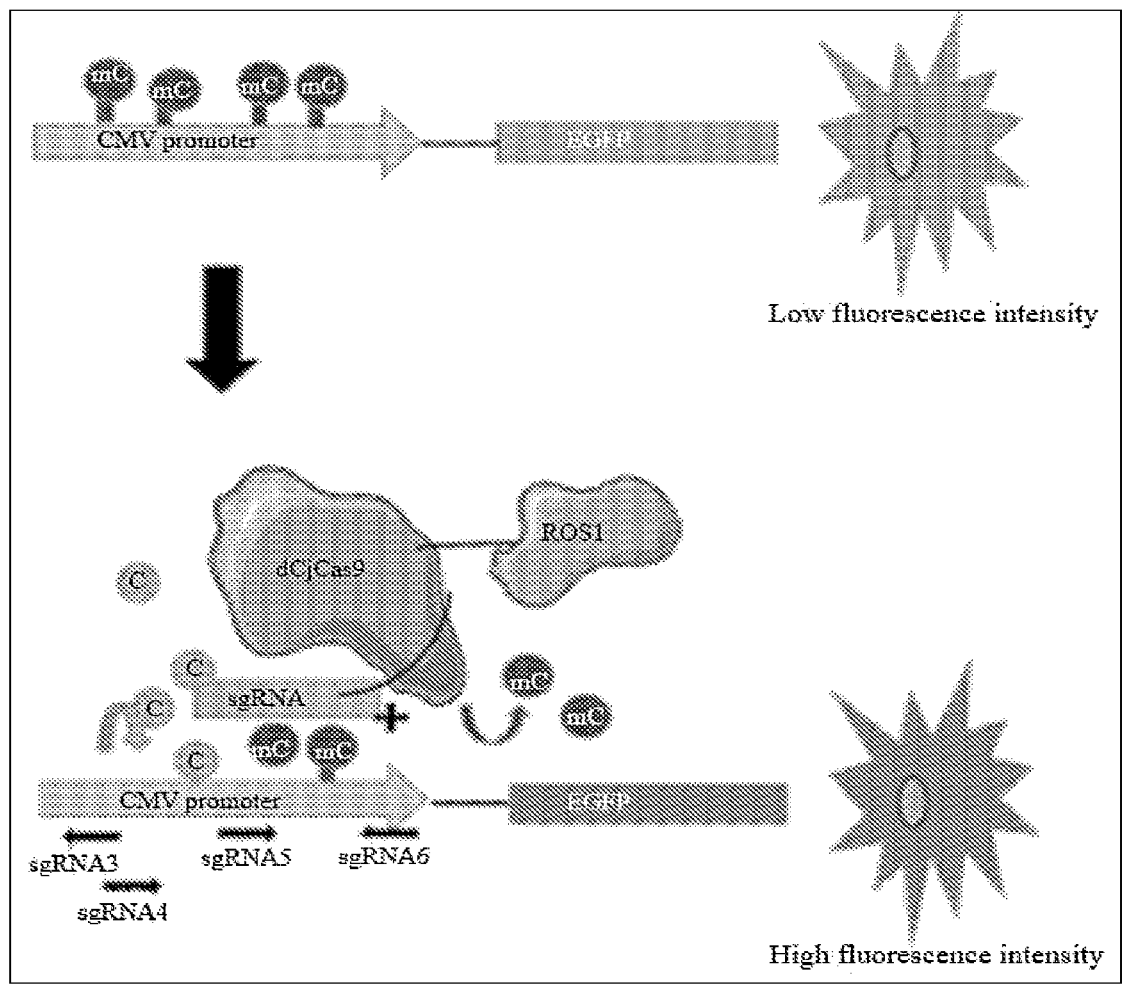
FIG. 5 illustrates a schematic diagram of demethylation test process.

The test idea of this embodiment is shown in FIG. 5. The promoter methylation gene could not be transcribed and expressed, and thus the expression of GFP in cells could not be observed when the pEGFP-N1 fluorescent reporter plasmid is 100% methylated. When the pEGFP-N1 fluorescent reporter plasmid is partially methylated, GFP is low expressed in cells. If Mini-CRISD can demethylate the promoter region, GFP can be re-expressed. Therefore, in this embodiment, the GFP fluorescence intensity is inversely linearly correlated to the degree of plasmid methylation.

Figure 6A:
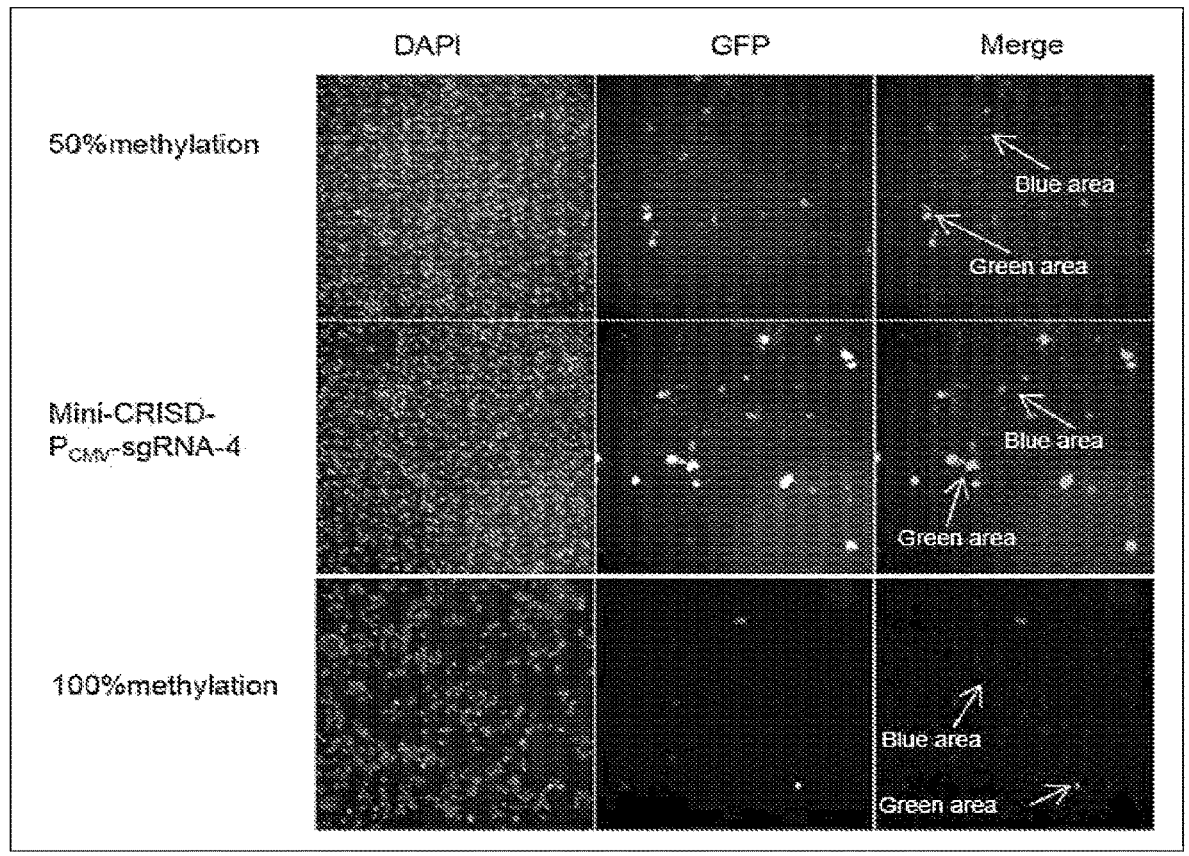
FIGS. 6A-6B illustrate demethylation effect of Mini-CRISD in embodiment 4.
Figure 6B:
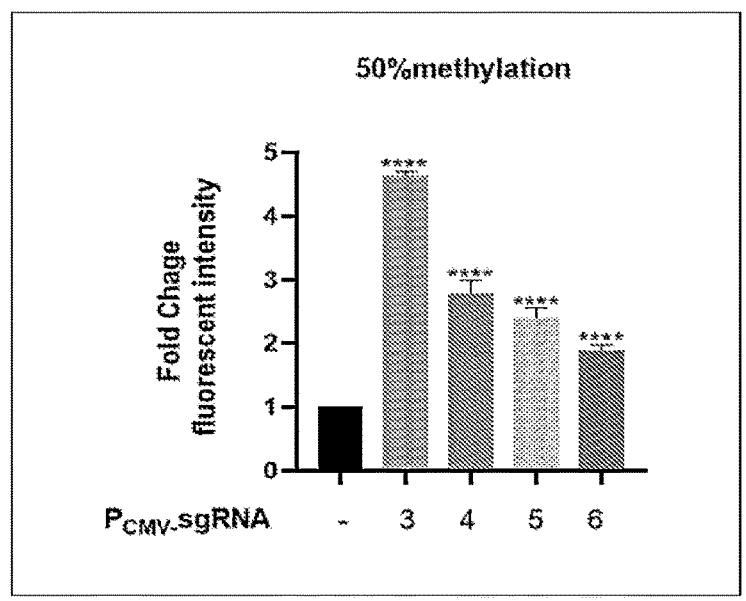

To quantify the demethylation effect of Mini-CRISD, the 50% methylated fluorescent reporter plasmid is taken as an example. As shown in FIGS. 6A-6B, the fluorescence intensity of 50% methylated fluorescent reporter plasmid in cells is very low. After the addition of Mini-CRISD, the expression and fluorescence intensity of GFP are significantly increased by demethylating the characteristics of CMV promoter region through Mini-CRISD under the guidance of sgRNA targeting the CMV promoter region. In the control group without sgRNA, the fluorescence intensity is not increased even with Mini-CRISD fusion protein. It is confirmed that the observed increase in GFP expression (that is, the fluorescence intensity is increased) is due to the demethylation of targeted DNA.

Embodiment 5

Methylated fluorescent reporter plasmids are tested for demethylation using the mini-CRISD method in 293T cells. The detailed steps are as follows.

1) 293T cells are uniformly inoculated into 96-well plates with a density of 12000 cells/well, and cultured in Dulbecco's modified eagle medium (DMEM) with higher glucose levels (containing 10% fetal bovine serum) in a constant temperature incubator at 37° C. and 5% $CO_2$.

2) After 24 hours, 50 ng each of the 75% methylated fluorescent reporter plasmid obtained from the embodiment 2 and Mini-CRISD expression plasmid (carrying one of Pcmv-sgRNA-3, Pcmv-sgRNA-4, Pcmv-sgRNA-5 and PcMv-sgRNA-6) obtained from the embodiment 3 are transfected into 293T cells simultaneously with lipofectamine 3000. The control group is simultaneously transfected with 50 ng of 75% methylated fluorescent reporter plasmid and 50 ng of Mini-CRISD-dead (demethylation inactivation mutation) plasmid are transfected simultaneously.

3) After 48 hours, the culture medium is removed, rinsed twice with PBS, and fixed with 4% paraformaldehyde. After 15 minutes, 4% paraformaldehyde is sucked out, and rinsed the PBS once. Then, 30 µL DAPI staining solution is added into each well. After 5 minutes, the staining solution is sucked out, rinsed twice with PBS, and 100 µL PBS is added into each well.

4) Image acquisition is performed using the Thermo Fisher Scientific CellInsight™ CX7-LZR high content analysis platform. 25 fields of view are selected in each well of 96-well plate, and the images are taken at 405 nm and 488 nm excitation wavelengths in each field of view. After DAPI staining, the nucleus is blue at 405 nm excitation wavelength, and the GFP expressed in cells is green at 488 nm excitation wavelength. The platform accurately locates the position of the nucleus by identifying the blue area, and identifies the cell range with the fixed value of the expansion of the nucleus. Then, 5 random fields of view of 25 fields are selected, the three wells are selected in the same way, and mean fluorescence intensity is calculated using ImageJ software, that is, mean fluorescence intensity (Mean)=sum of fluorescence intensities of this region (IntDen)/Area of this region (Area).

Figure 7A:
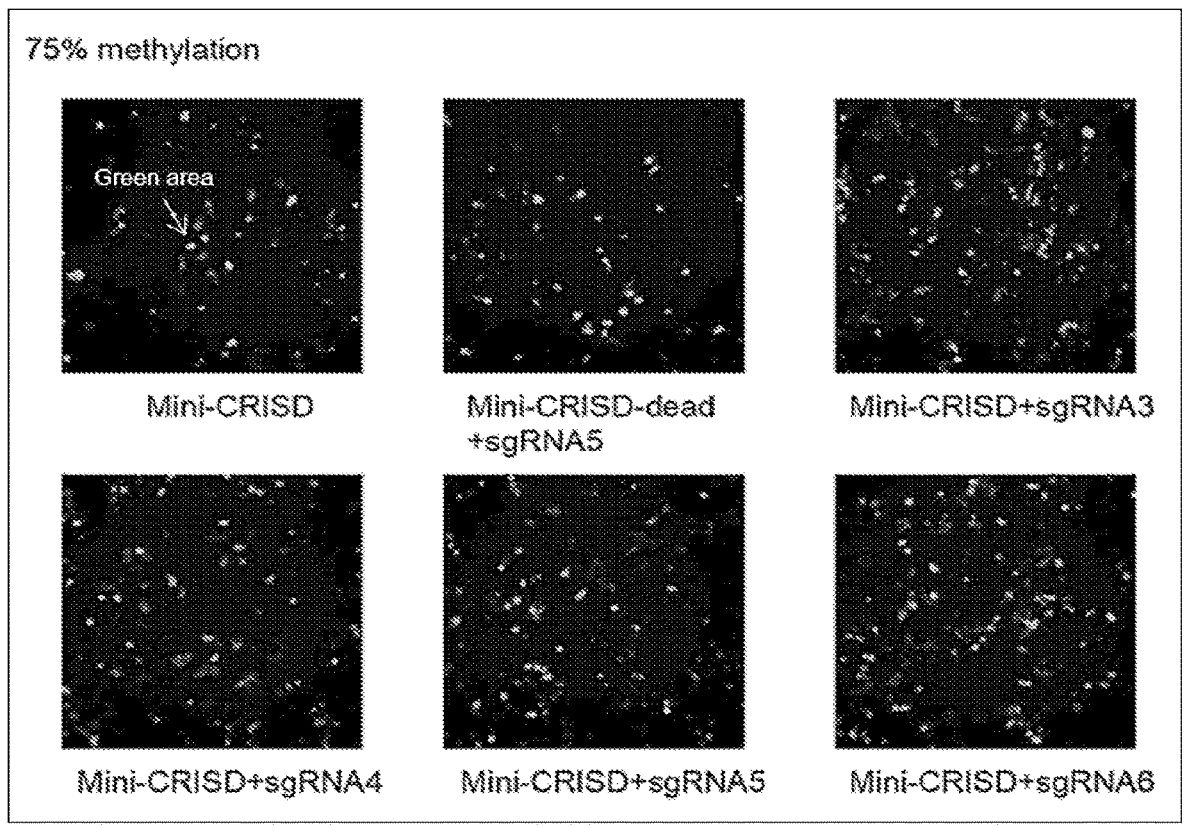
FIGS. 7A-7B illustrate demethylation effect of Mini-CRISD in embodiment 5.
Figure 7B:
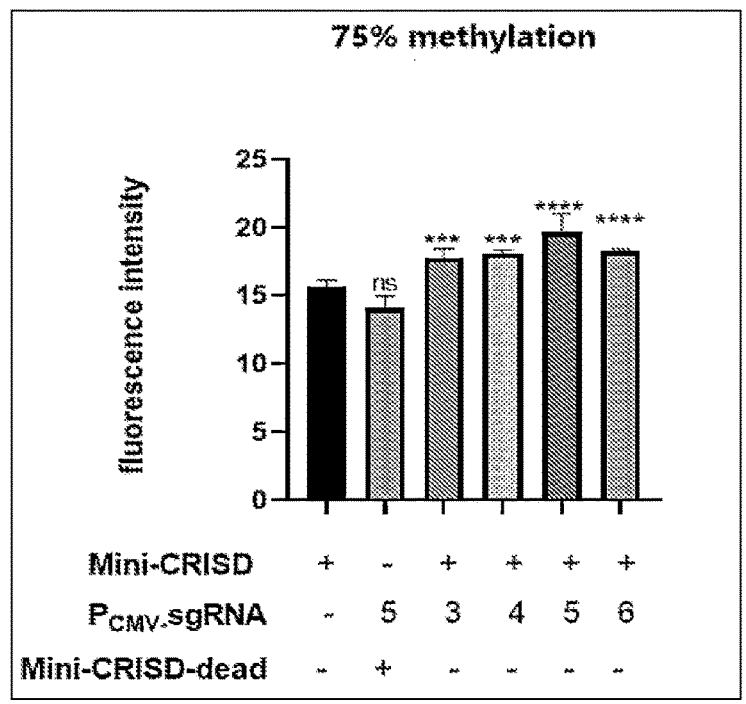

To quantify the demethylation effect of Mini-CRISD, the 75% methylated fluorescent reporter plasmid is taken as an example. As shown in FIGS. 7A-7B, the fluorescence intensity of 75% methylated fluorescent reporter plasmid in cells is low. After the addition of Mini-CRISD, the expression and fluorescence intensity of GFP are significantly increased by demethylating the characteristics of CMV promoter region through Mini-CRISD under the guidance of sgRNA targeting the CMV promoter region. However, Mini-CRISD-dead does not exhibit increased fluorescence intensity even with the addition of targeted promoter sgRNA due to inactivation of the demethylated active site, further confirming that the observed increase in GFP expression (i.e., increased fluorescence intensity) is due to targeted DNA demethylation.

Embodiment 6

The promoter region of the tumor suppressor gene Ras association domain family 1A (RASSF1A) is targeted for demethylation by the Mini-CRISD method, thereby increasing the expression level of RASSF1A in lung cancer cells. The following steps are included.

Figure 8:
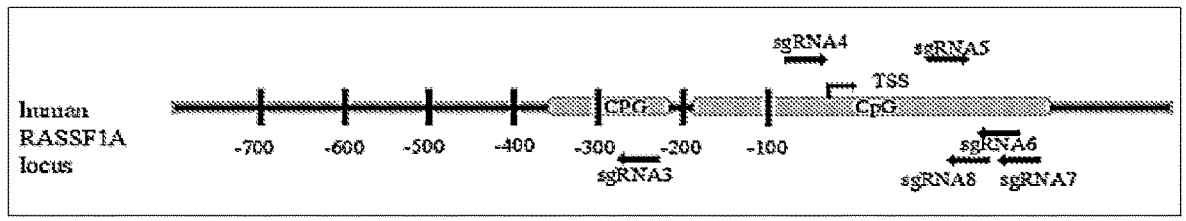
FIG. 8 illustrates a schematic diagram showing relative positions of DNA target on genome and a tumor suppressor gene Ras association domain family 1A (RASSF1A) promoter in embodiment 6.

1) A Mini-CRISD plasmid targeting RASSF1A promoter in human genome is constructed. 6 recognition sequences on the RASSF1A promoter that meet the requirements of CjCas9 PAM sequence (see the following table) are selected, and the relative positions of DNA targets on the genome and RASSF1A promoter are shown in FIG. 8. In this situation, $P_{RASSF1A}$-sgRNA-8 uses the 5'-ACA-3' PAM site, and the rest of the sgRNAs use the 5'-NNNVRYAC-3' PAM site.

According to the same construction method as in the embodiment 3, the blank sequences on the Mini-CRISD plasmid vector are replaced with the above recognition sequences, thereby obtaining six Mini-CRISD expression plasmids targeting the human tumor suppressor gene RASSF1A promoter (carrying sgRNA targeting the human tumor suppressor gene RASSF1A promoter).

| | | |
|---|---|---|
| $P_{RASSF1A}$-SgRNA-3 | TTCCTTCCCTCCTTCGTCCCCT | (SEQ ID NO: 15) |
| $P_{RASSF1A}$-SgRNA-4 | GCTTGCTAGCGCCCAAAGCCAG | (SEQ ID NO: 16) |
| $P_{RASSF1A}$-SgRNA-5 | CTGAGCTCATTGAGCTGCGGGA | (SEQ ID NO: 17) |
| $P_{RASSF1A}$-SgRNA-6 | CCCCAGATGAAGTCGCCACAGA | (SEQ ID NO: 18) |
| $P_{RASSF1A}$-SgRNA-7 | TGCGACAAGGGATAAACCATTT | (SEQ ID NO: 19) |
| $P_{RASSF1A}$-SgRNA-8 | CCAGGGACCAGCTGCCGTGTGG | (SEQ ID NO: 20) |

2. Culture of human lung cancer cells A549 and H1299

A549 cells are uniformly inoculated into 6-well plates with a density of 25000 cells/well, using Ham's F-12K medium (containing 10% fetal bovine serum). H1299 cells are uniformly inoculated into 6-well plates with a density of 30000 cells/well, using Roswell Park Memorial Institute (RPMI)-1640 medium (containing 10% fetal bovine serum). Then, the A549 cells and the H1299 cells are cultured in a constant temperature incubator at 37° C. and 5% $CO_2$.

3. Detection of demethylation of RASSF1A promoter and RASSF1A expression in human lung cancer cells.

After 24 hours, the medium is replaced with fresh medium and transfected. 1 ug Mini-CRISD expression plasmid (carrying one of $P_{RASSF1A}$-sgRNA-3, $P_{RASSF1A}$-sgRNA-4, $P_{RASSF1A}$-sgRNA-5, $P_{RASSF1A}$-sgRNA-6, $P_{RASSF1A}$-sgRNA-7, $P_{RASSF1A}$-sgRNA-8) is transfected into A549 cells or H1299 cells by using lipofectamine 3000. After 6 hours, the medium is replaced with a new medium. The control group is transfected with 1 ug of the Mini-CRISD-dead (demethylation inactivation mutation) plasmid.

In the A549 cell experiment, dicitabine, a small molecule inhibitor of DNA methylation, is used as a group of positive controls. Dicitabine (Sigma, Article No. A3656) is dissolved in dimethyl sulfoxide (DMSO) to make a 10 mM mother solution, 2 uL of dicitabine mother solution is added into every 2 mL of cell culture medium, so that the final concentration of decitabine is 10 uM, and a new medium containing decitabine is replaced every 24 hours.

After 48-72 hours, total RNA of transfected cells is extracted using SteadyPure universal RNA extraction kit (Guangzhou Ruizhen Biotechnology Co., Ltd, Article No. AG21022), and RT-qPCR experiments are performed to detect the expression of RASSF1A gene using Evo M-MLV reverse transcription kit (Guangzhou Ruizhen Biotechnology Co., Ltd, Article No. AG11711) and SYBR Green® Pro Taq HS premix-type qPCR kit (Guangzhou Ruizhen Biotechnology Co., Ltd, Article No. AG11702). The primers for detecting RASSF1A by qPCR are GAAGTCATT-GAGGCCTGCT as shown in SEQ ID NO: 31 and ATCATC-CAACAGCTTCCGCGCA as shown in SEQ ID NO: 32.

Figure 9A:
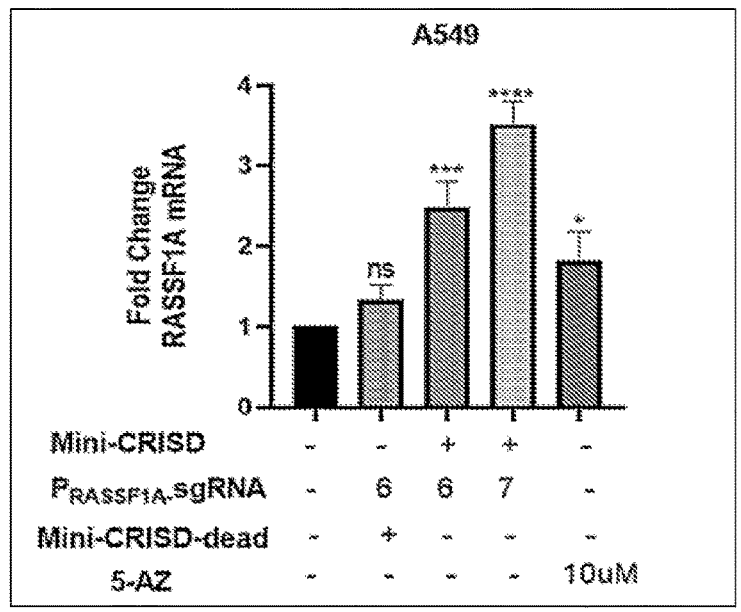
FIGS. 9A-9B illustrate demethylation effect of a promoter region of the tumor suppressor gene RASSF1A in the embodiment 6.
Figure 9B:
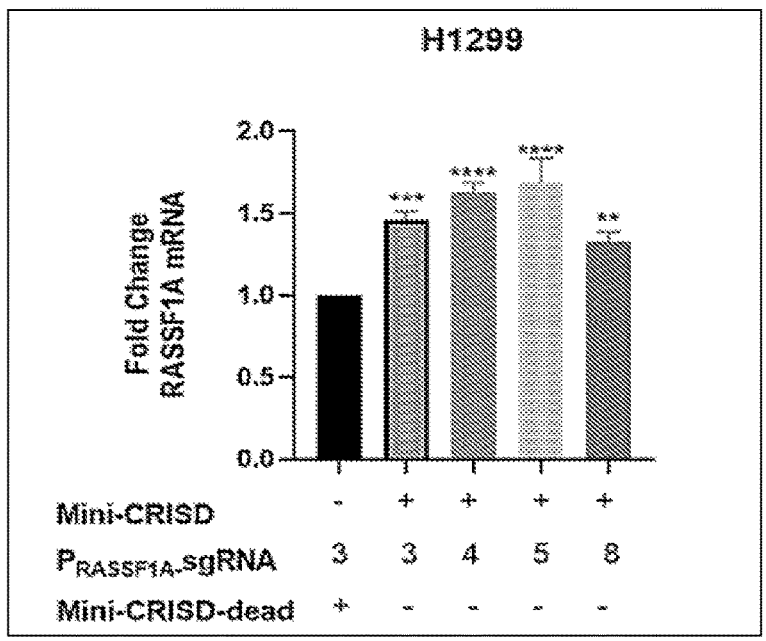

As shown in FIGS. 9A-9B, Mini-CRISD targets the promoter region of the tumor suppressor gene RASSF1A in A549 and H1299 cells and demethylates the promoter region, which significantly enhances the RASSF1A gene in lung cancer cells and promotes the expression of RASSF1A gene. The effect of Mini-CRISD targeted demethylation (based on the increase of RASSF1A gene expression level) is significantly better than that of non-targeted small molecule inhibitor (dicitabine).

Embodiment 7

The expression level of tumor suppressor gene RASSF1A is targeted by Mini-CRISD method to promote the death of lung cancer cells.

1. 1 ug Mini-CRISD expression plasmid (carrying $P_{RASSF1A}$-sgRNA-7) is transfected into A549 lung cancer cells according to the same method in the embodiment 6. After 48-72 hours of transfection, A549 cells are detected by Calcein-acetoxymethyl ester (Calcein-AM)/propidium iodide (PI) live/dead cell double staining.

2. 10× Assay Buffer is taken out from the low-temperature refrigerator and diluted 10-fold with deionized water to obtain 1× Assay Buffer. 5 μL Calcein-AM solution (2 mM) and 15 μL PI solution (1.5 mM) are taken and added into 1× Assay Buffer, and fully mixed to obtain a staining solution.

3. The culture medium is removed, the cells are rinsed twice with PBS, and the cells are rinsed twice with 1× Assay Buffer. 500 μL staining working solution is taken and added into a center of a confocal dish of adhered cells, and incubated for 15 minutes at 37° C. in the dark.

4. The living cells (green fluorescence) are detected with excitation light at 488 nm and the dead cells (red fluorescence) are detected with excitation light at 535 nm under a laser scanning confocal microscope. Calcein-AM itself does not fluoresce, but is cleaved by cellular lactonase to form membrane-impermeable Calcein which is retained in the cell and emits strong green fluorescence after entering the cell, while dead cells lack esterase activity, so that Calcein-AM only labels living cells. Propidium iodide (PI) cannot pass through the cell membrane of living cells, but can only pass through the cell membrane of dead cells to reach the nucleus and insert the double helix of cell DNA to produce red fluorescence, and thus PI only marks dead cells.

Figure 10A:
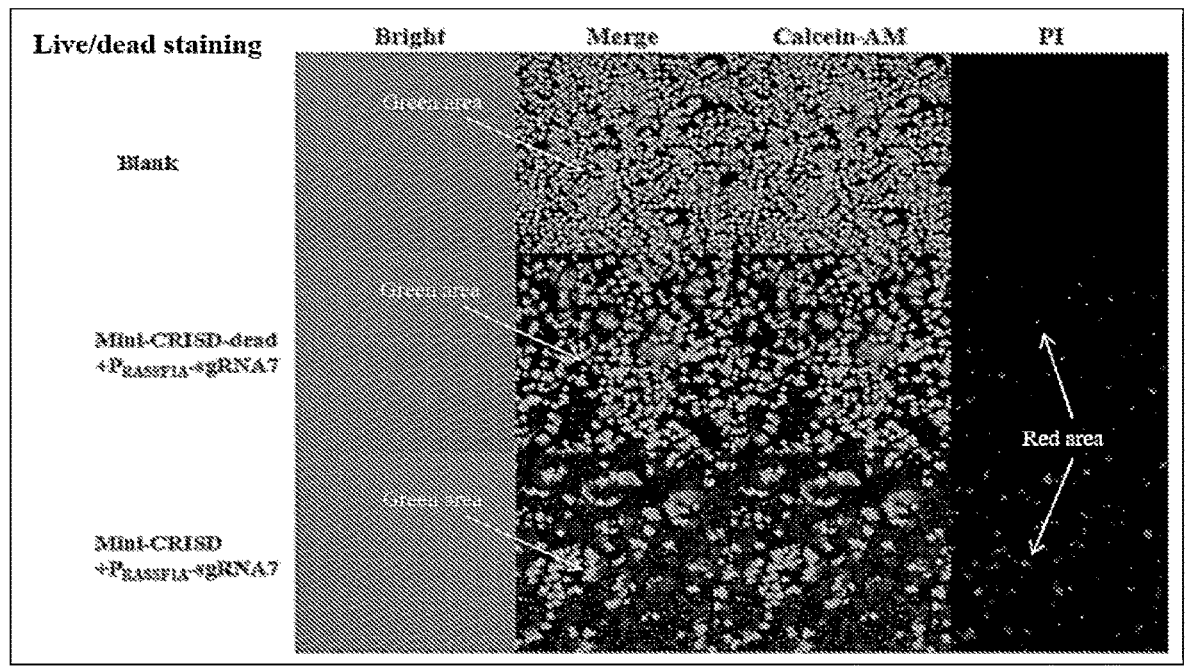
FIGS. 10A-10B illustrate demethylation effect of the promoter region of the tumor suppressor gene RASSF1A in embodiment 7.
Figure 10B:
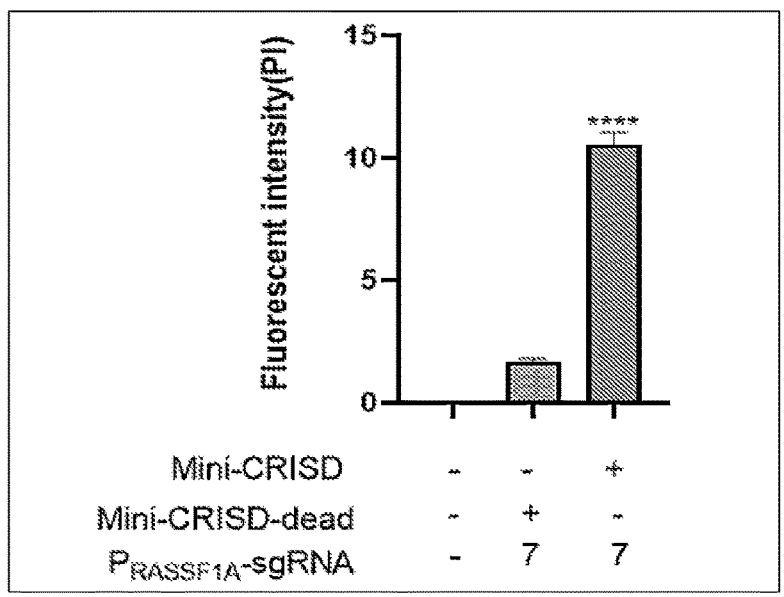

As shown in FIGS. 10A-10B, Mini-CRISD targets the promoter region of the tumor suppressor gene RASSF1A in A549 cells and demethylates the promoter region, promoting the expression of RASSF1A gene, thus causing the death of A549 cells, which is significantly different from the control group Mini-CRISD-dead group and the non-transfected group.

The above embodiments only show several embodiments of the disclosure, and the description is more specific and detailed, but it should not be understood as limiting the scope of the disclosure. It should be pointed out that for those skilled in the art, certain modifications and changes can be made without departing from the concept of the disclosure, which belong to the protection scope of the disclosure. Therefore, the scope of protection of the disclosure patent shall be subject to the appended claims.

What is claimed is:

1. A fusion protein, comprising:
a truncated *Campylobacter jejuni* clustered regularly interspaced short palindromic repeat associated endonuclease 9 (CjCas9) and a truncated repressor of silencing 1 (ROS1) connected by an intermediate sequence comprising a linker;
wherein the truncated CjCas9 is an amino acid fragment obtained by removing amino acids at positions 481-640 of a CjCas9 protein, connecting remaining amino acids with a linker, and performing D8A point mutation; and
wherein the truncated ROS1 is an amino acid fragment obtained by removing amino acids at positions 1-509 and 628-855 of a ROS1 protein and connecting remaining amino acids with a linker, and an amino acid at position 971 of the ROS1 protein is aspartic acid;
wherein the fusion protein from an N-terminal to a C-terminal sequentially comprises:
the preamble sequence shown in SEQ ID NO: 24;
the sequence shown in SEQ ID NO:1, the linker shown in SEQ ID NO: 27, and the sequence shown in SEQ ID NO:2;
the intermediate sequence shown in SEQ ID NO: 23; and
the sequence shown in SEQ ID NO: 3, the linker shown in SEQ ID NO: 26, and the sequence shown in SEQ ID NO: 4.

2. A nucleotide sequence encoding the fusion protein according to claim 1.

3. An expression vector containing a nucleotide sequence encoding the fusion protein of claim 1.

4. The expression vector according to claim 3, wherein the expression vector carries a DNA nucleotide sequence for expressing single guide RNAs (sgRNAs), and each of sgRNA sequences comprises a skeleton sequence and a recognition sequence for recognizing a target DNA.

5. A kit for targeted DNA demethylation, comprising the expression vector according to claim 4.

6. A method of inducing at least one of ex vivo DNA demethylation and in vitro DNA demethylation comprising introducing the expression vector according to claim 4 into human or animal cells.

7. A kit for targeted DNA demethylation, comprising the fusion protein according to claim 1.

8. A method of inducing at least one of ex vivo DNA demethylation and in vitro DNA demethylation comprising introducing the fusion protein according to claim 1 into human or animal cells along with a sgRNA that comprises a skeleton sequence and a recognition sequence for recognizing a target DNA.

9. A fusion protein, wherein the amino acid sequence of the fusion protein is sequentially composed of:
the sequence shown in SEQ ID NO: 24;
the sequence shown in SEQ ID NO:1;
the sequence shown in SEQ ID NO: 27;
the sequence shown in SEQ ID NO:2;
the sequence shown in SEQ ID NO: 23;
the sequence shown in SEQ ID NO: 3;
the sequence shown in SEQ ID NO: 26; and
the sequence shown in SEQ ID NO: 4.

* * * * *

SEQUENCE LISTING

```
Sequence total quantity: 32
SEQ ID NO: 1            moltype = AA  length = 480
FEATURE                 Location/Qualifiers
source                  1..480
                        mol_type = protein
                        organism = synthetic construct
SEQUENCE: 1
MARILAFAIG ISSIGWAFSE NDELKDCGVR IFTKVENPKT GESLALPRRL ARSARKRLAR  60
RKARLNHLKH LIANEFKLNY EDYQSFDESL AKAYKGSLIS PYELRFRALN ELLSKQDFAR 120
VILHIAKRRG YDDIKNSDDK EKGAILKAIK QNEEKLANYQ SVGEYLYKEY FQKFKENSKE 180
FTNVRNKKES YERCIAQSFL KDELKLIFKK QREFGFSFSK KFEEEVLSVA FYKRALKDFS 240
HLVGNCSFFT DEKRAPKNSP LAFMFVALTR IINLLNNLKN TEGILYTKDD LNALLNEVLK 300
NGTLTYKQTK KLLGLSDDYE FKGEKGTYFI EFKKYKEFIK ALGEHNLSQD DLNEIAKDIT 360
LIKDEIKLKK ALAKYDLNQN QIDSLSKLEF KDHLNISFKA LKLVTPLMLE GKKYDEACNE 420
LNLKVAINED KKDFLPAFNE TYYKDEVTNP VVLRAIKEYR KVLNALLKKY GKVHKINIEL 480

SEQ ID NO: 2            moltype = AA  length = 344
FEATURE                 Location/Qualifiers
source                  1..344
                        mol_type = protein
                        organism = synthetic construct
SEQUENCE: 2
RYIARLVLNY TKDYLDFLPL SDDENTKLND TQKGSKVHVE AKSGMLTSAL RHTWGFSAKD  60
RNNHLHHAID AVIIAYANNS IVKAFSDFKK EQESNSAELY AKKISELDYK NKRKFFEPFS 120
GFRQKVLDKI DEIFVSKPER KKPSGALHEE TFRKEEEFYQ SYGGKEGVLK ALELGKIRKV 180
NGKIVKNGDM FRVDIFKHKK TNKFYAVPIY TMDFALKVLP NKAVARSKKG EIKDWILMDE 240
NYEFCFSLYK DSLILIQTKD MQEPEFVYYN AFTSSTVSLI VSKHDNKFET LSKNQKILFK 300
NANEKEVIAK SIGIQNLKVF EKYIVSALGE VTKAEFRQRE DFKK             344
```

```
SEQ ID NO: 3                moltype = AA  length = 118
FEATURE                     Location/Qualifiers
source                      1..118
                            mol_type = protein
                            organism = synthetic construct
SEQUENCE: 3
GAGAIVPVTP VKKPRPRPKV DLDDETDRVW KLLLENINSE GVDGSDEQKA KWWEEERNVF   60
RGRADSFIAR MHLVQGDRRF TPWKGSVVDS VVGVFLTQNV SDHLSSSAFM SLASQFPV    118

SEQ ID NO: 4                moltype = AA  length = 538
FEATURE                     Location/Qualifiers
source                      1..538
                            mol_type = protein
                            organism = synthetic construct
SEQUENCE: 4
AFDWDCLRRE AQARAGIREK TRSTMDTVDW KAIRAADVKE VAETIKSRGM NHKLAERIQG   60
FLDRLVNDHG SIDLEWLRDV PPDKAKEYLL SFNGLGLKSV ECVRLLTLHH LAFPVDTNVG  120
RIAVRLGWVP LQPLPESLQL HLLEMYPMLE SIQKYLWPRL CKLDQKTLYE LHYQMITFGK  180
VFCTKSKPNC NACPMKGECR HFASAFASAR LALPSTEKGM GTPDKNPLPL HLPEPFQREQ  240
GSEVVQHSEP AKKVTCCEPI IEEPASPEPE TAEVSIADIE EAFFEDPEEI PTIRLNMDAF  300
TSNLKKIMEH NKELQDGNMS SALVALTAET ASLPMPKLKN ISQLRTEHRV YELPDEHPLL  360
AQLEKREPDD PCSYLLAIWT PGETADSIQP SVSTCIFQAN GMLCDEETCF SCNSIKETRS  420
QIVRGTILIP CRTAMRGSFP LNGTYFQVNE VFADHASSLN PINVPRELIW ELPRRTVYFG  480
TSVPTIFKGL STEKIQACFW KGYVCVRGFD RKTRGPKPLI ARLHFPASKL KGQQANLA   538

SEQ ID NO: 5                moltype = AA  length = 1542
FEATURE                     Location/Qualifiers
source                      1..1542
                            mol_type = protein
                            organism = synthetic construct
SEQUENCE: 5
ATMDYKDDDD KSPKKKRKVE ASARILAFAI GISSIGWAFS ENDELKDCGV RIFTKVENPK   60
TGESLALPRR LARSARKRLA RRKARLNHLK HLIANEFKLN YEDYQSFDES LAKAYKGSLI  120
SPYELRFRAL NELLSKQDFA RVILHIAKRR GYDDIKNSDD KEKGAILKAI KQNEEKLANY  180
QSVGEYLYKE YFQKFKENSK EFTNVRNKKE SYERCIAQSF LKDELKLIFK KQREFGFSFS  240
KKFEEEVLSV AFYKRALKDF SHLVGNCSFF TDEKRAPKNS PLAFMFVALT RIINLLNNLK  300
NTEGILYTKD DLNALLNEVL KNGTLTYKQT KKLLGLSDDY EFKGEKGTYF IEFKKYKEFI  360
KALGEHNLSQ DDLNEIAKDI TLIKDEIKLK KALAKYDLNQ NQIDSLSKLE FKDHLNISFK  420
ALKLVTPLML EGKKYDEACN ELNLKVAINE DKKDFLPAFN ETYYKDEVTN PVVLRAIKEY  480
RKVLNALLKK YGKVHKINIE LGGGSGGRYI ARLVLNYTKD YLDFLPLSDD ENTKLNDTQK  540
GSKVHVEAKS GMLTSALRHT WGFSAKDRNN HLHHAIDAVI IAYANNSIVK AFSDFKKEQE  600
SNSAELYAKK ISELDYKNKR KFFEPFSGFR QKVLDKIDEI FVSKPERKKP SGALHEETFR  660
KEEEFYQSYG GKEGVLKALE LGKIRKVNGK IVKNGDMFRV DIFKHKKTNK FYAVPIYTMD  720
FALKVLPNKA VARSKKGEIK DWILMDENYE FCFSLYKDSL ILIQTKDMQE PEFVYYNAFT  780
SSTVSLIVSK HDNKFETLSK NQKILFKNAN EKEVIAKSIG IQNLKVFEKY IVSALGEVTK  840
AEFRQREDFK KSPKKKRKVE ASKLGGGGSG GGGSGGGGSV DGAGAIVPVT PVKKPRPRPK  900
VDLDDETDRV WKLLLENINS EGVDGSDEQK AKWWEEERNV FRGRADSFIA RMHLVQGDRR  960
FTPWKGSVVD SVVGVFLTQN VSDHLSSSAF MSLASQFPVG SSGNAFDWDC LRREAQARAG 1020
IREKTRSTMD TVDWKAIRAA DVKEVAETIK SRGMNHKLAE RIQGFLDRLV NDHGSIDLEW 1080
LRDVPPDKAK EYLLSFNGLG LKSVECVRLL TLHHLAFPVN TNVGRIAVRL GWVPLQPLPE 1140
SLQLHLLEMY PMLESIQKYL WPRLCKLDQK TLYELHYQMI TFGKVFCTKS KPNCNACPMK 1200
GECRHFASAF ASARLALPST EKGMGTPDKN PLPLHLPEPF QREQGSEVVQ HSEPAKKVTC 1260
CEPIIEEPAS PEPETAEVSI ADIEEAFFED PEEIPTIRLN MDAFTSNLKK IMEHNKELQD 1320
GNMSSALVAL TAETASLPMP KLKNISQLRT EHRVYELPDE HPLLAQLEKR EPDDPCSYLL 1380
AIWTPGETAD SIQPSVSTCI FQANGMLCDE ETCFSCNSIK ETRSQIVRGT ILIPCRTAMR 1440
GSFPLNGTYF QVNEVFADHA SSLNPINVPR ELIWELPRRT VYFGTSVPTI FKGLSTEKIQ 1500
ACFWKGYVCV RGFDRKTRGP KPLIARLHFP ASKLKGQQAN LA                  1542

SEQ ID NO: 6                moltype = DNA  length = 4623
FEATURE                     Location/Qualifiers
source                      1..4623
                            mol_type = other DNA
                            organism = synthetic construct
SEQUENCE: 6
atggattaca aggacgacga tgacaagtcg ccgaagaaaa agcgcaaggt cgaagcgtcc   60
atggctcgca ttctggcttt tgctattgga atcagtagca ttggatgggc ttttctgag  120
aacgacgagc tgaaggattg cggggtgaga ttttttacta aggtagagaa cccaaagacc  180
ggagagagtc tcgccctgcc ccgacggctg gccaggagtg ctcgcaaaag gctggccgag  240
cgcaaagcca ggctgaacca tctcaagcac cttatcgcca acgagtttaa gctcaactat  300
gaagattacc aaagttttga tgagagtctg gcgaaagcct ataagggttc attgatttca  360
ccctatgagc tgcgcttccg cgcgctgaat gagttgctga gtaagcaaga cttcgcacgg  420
gttatcctgc acattgcaaa aaggcgcggg tacgatgaca ttaagaactc agacgacaag  480
gagaaggggg ccatcttgaa ggccatcaaa cagaatgaag aagctcgc aaactaccag  540
tctgtgggcg agtatcttta caaagagtac tttcagaagt tcaaagaaaa cagtaaagaa  600
tttactaacg ttcggaataa gaaggagagc tatgagcgct gcattgccca gtctttcctg  660
aaggacgaac tcaagctgat tttcaagaaa cagcgcgaat tggtttcag cttttcaaa  720
aagttcgaag aagaggtcct gagtgtggcc ttttacaagc gggctctgaa agacttcagt  780
catctggttg gcaattgctc attttcacc gatgaaaagc gcgcccctaa aaactcaccc  840
```

```
                                  -continued
ctcgctttta tgttcgtggc cctgactagg atcataaatc tgctgaacaa cctgaaaaat   900
accgagggaa tcctctacac taaggatgat cttaacgctc tgctgaacga ggttctgaag   960
aatgggaccc tgacctataa acagaccaag aagctcctcg ggttgagcga tgattatgag  1020
tttaagggcg aaaagggcac ctattttatt gagttcaaaa agtacaagga atttatcaaa  1080
gccctgggag aacacaattt gagtcaagat gatctgaatg aaatcgccaa agacattact  1140
ctgatcaagg acgaaattaa gctgaagaag gctttggcaa aatacgatct gaatcaaaat  1200
caaatcgatt cactgagtaa actggaattt aaagaccacc ttaatataag tttcaaagcg  1260
ttgaaactgg tgaccccact gatgctcgaa ggtaagaaat atgacgaagc tgcaacgaa   1320
ctgaatctga aagtggcaat taacgaagat aaaaaggact tcttgccagc cttcaatgaa  1380
acttattaca aagatgaagt taccaatccg gtcgtgttgc gcgctatcaa ggagtatcgg  1440
aaggtgctga atgccctgct gaaaaaatat gggaaagtgc acaaaatcaa cattgagctt  1500
ggaggtggca gtggcgggcg gtacatagcc agactcgttt tgaactatac aaaagactac  1560
ctggacttcc tgccctgag tgacgatgaa aacaccaaac tgaacgacac acaaaaaggt  1620
agcaaggtgc acgtagaggc caaatcaggt atgctcacga gcgcccttcg ccatacatgg  1680
ggttttagcg ctaaggaccg caacaatcat ctgcaccatg ccattgacgc tgtgattata  1740
gcctacgcca ataactctat cgtgaaggca ttcagcgact ttaagaagga gcaggagtcc  1800
aattctgccg agttgtacgc aaaaaaaatc tcagaactcg attacaagaa caaaagaaag  1860
ttctttgagc cattcagcgg atttagacag aaagtttttg acaagatcga tgagatttc   1920
gtgtctaagc ccgagagaaa gaagccttcc ggcgcattgc acgaagaaac cttcagaaaa  1980
gaggaagagt tttaccagtc atatggaggc aaggagggcg tacttaaggc tctggagctt  2040
ggaaagatta ggaaggtcaa tggtaaaatt gtgaagaatg agacatgtt tagggtcgat   2100
atatttaagc acaaaaagac caatgaaatt tacgccgtcc caatctatac gatgactt     2160
gcactgaagg tcttgcccaa caaggcagtc gctcgcagca aaaaagggga gattaaggat  2220
tggattctga tggatgagaa ttatgagttt gctttagcc tctacaagga ttctctgatc   2280
ttgattcaaa caaaagacat gcaggagccc gagttcgtgt actacaacgc cttcacttct  2340
agtacagtga gtctgatcgt gtctaagcac gacaacacat tcgagaccct cagcaagaac  2400
cagaagatcc tgtttaagaa cgcaaacgag aaggaagtga ttgcaaagag catcggcata  2460
cagaatttga aagttttga aaaatacatt gtctccgcac tcggcgaggt taccaaagcc   2520
gagtttcggc agagggagga tttcaagaaa agccccaaga gaagagaaa ggtggaggcc   2580
agcaagcttg gaggcggcgg tagccgagga ggcgggtccg gcggcggcgg tagtgtcgac  2640
ggcgcaggtg caatagtacc tgtgacacca gttaagaaac cccgaccaag gcctaaagtg  2700
gacctcgatg atgaaacgga tagagtgtgg aagctcctgc tggagaacat aaactctgaa  2760
ggcgtcgatg gagcgacga acaaaaggcc aaatggtggg aggaggaacg aaacgttttt   2820
aggggacgag cggactcatt catcgctcgc atgcacctgg tgcaaggga caggaggttc   2880
actccatgga agggctccgt agtggactca gttgtgggag tgtttttgac ccagaacgtg  2940
agcgaccacc tcagttcttc agccttcatg tctctggcta gtcaattccc tgtttgggtcc  3000
agcggcaacg catttgactg ggactgtctt aggcgcgaag cccaggctag ggcaggtatt  3060
cgagaaaaga cccgctcaac catggatacc gtggattgga aagcaattag agccgcggat  3120
gttaaggagg ttgcagaaac catcaagtcc agggaatga atcacaagct cgctgaaagg  3180
attcaagggt tccttgaccg cctcgtgaat gaccatggca gtatcgatct ggaatgcgta  3240
agggacgtgc cccctgataa agccaaagaa tacttgcttt cttcaatgg gttggggctg   3300
aaaatccgtg agtgtgtacg gctgttgaca ctccaccact tggcattccc agtggacaca  3360
aacgttggaa ggatcgctgt cagactcggt tgggtgcctc tgcagcctct tccagaaagc  3420
ctccaacttc acctgttgga gatgtatcct atgctgaat caatccagaa atacctgtgc  3480
ccacgccttt gcaagctgga ccagaaaaca ctgtatgaat tgcactatca gatgatcacc  3540
tttggtaaag ttttctgtac caagtccaag ccaaactgta atgcttgtcc gatgaaaggg  3600
gagtgtcgcc atttcgcctc tgcctttgca agcgccagac tggcactcct aagcaccgag  3660
aagggcatgg gaactcccga taaaaacct ttgcctctgc acctgcctga gcccttccaa   3720
agagagcagg ggagcgaagt ggtccagcat tctgaacctg ccaagaaagt aacctgttgc  3780
gaaccaatca ttgaagagcc tgccagtcct gaaccagaga cagcagaggt gagcatcgcc  3840
gatattggag aagcctttt cgaagatccc gaagagatcc tccaccattcg gctgaacatg  3900
gacgccttca caagtaacct caagaaaatt atgaacata caaggaact ccaggacggg    3960
aatatgagca gtgcccctggt ggctctgaca gccgaaacag caagtctgcc catgcctaag  4020
ttgaagaaca tttcacagct tcggaccgag catagggttt atgagctgcc agatgagcac  4080
ccactgctgg ctcagttgga gaaacgccaa ccagacgatc catgcagtta cctgctggca  4140
atctggacac cgggtgagac agcagacagc attcagccat cagtatctac ctgcatattt  4200
caggcaaatg ggatgttgtg cgacgaggaa acatgtttta gttgcaattc tatcaaggag  4260
accagaagtc agattgtgcg cggcactatt ctcatacct gtcgaacagc aatgcgcggt   4320
tcatttccac tcaacggcac atacttccag gtcaatgaag tgttgccga tcatgcttcc   4380
agcctgaatc ctattaatgt tccacggaga ttgatatggg agcttccccg acgcaccgtc  4440
tatttggta catccgtccc taccatcttc aaaggactct caaccgagaa gattcaagcc  4500
tgttttggaa aggggtacgt ttgcgtgaga ggatttgaca gaaagactag ggggcctaaa  4560
cctcttatag cccgcctgca cttcctgcc tctaagctga agggccaaca agctaacttg   4620
gcc                                                                4623

SEQ ID NO: 7               moltype = AA   length = 984
FEATURE                    Location/Qualifiers
source                     1..984
                           mol_type = protein
                           organism = synthetic construct
SEQUENCE: 7
MARILAFDIG ISSIGWAFSE NDELKDCGVR IFTKVENPKT GESLALPRRL ARSARKRLAR   60
RKARLNHLKH LIANEFKLNY EDYQSFDESL AKAYKGSLIS PYELRFFRALN ELLSKQDFAR  120
VILHIAKRRG YDDIKNSDDK EKGAILKAIK QNEEKLANYQ SVGEYLYKEY FQKFKENSKE   180
FTNVRNKKES YERCIAQSFL KDELKLIFKK QREFGSFSK KFEEEVLSVA FYKRALKDFS    240
HLVGNCSFFT DEKRAPKNSP LAFMFVALTR IINLLNNLKN TEGILYTKDD LNALLNEVLK   300
NGTLTYKQTK KLLGLSDDYE FKGEKGTYFI EFKKYKEFIK ALGEHNLSQD DLNEIAKDIT   360
LIKDEIKLKK ALAKYDLNQN QIDSLSKLEF KDHLNISFKA LKLVTPLMLE GKKYDEACNE   420
LNLKVAINED KKDFLPAFNE TYYKDEVTNP VVLRAIKEYR KVLNALLKKY GKVHKINIEL   480
```

```
AREVGKNHSQ RAKIEKEQNE NYKAKKDAEL ECEKLGLKIN SKNILKLRLF KEQKEFCAYS    540
GEKIKISDLQ DEKMLEIDHI YPYSRSFDDS YMNKVLVFTK QNQEKLNQTP FEAFGNDSAK    600
WQKIEVLAKN LPTKKQKRIL DKNYKDKEQK NFKDRNLNDT RYIARLVLNY TKDYLDFLPL    660
SDDENTKLND TQKGSKVHVE AKSGMLTSAL RHTWGFSAKD RNNHLHHAID AVIIAYANNS    720
IVKAFSDFKK EQESNSAELY AKKISELDYK NKRKFFEPFS GFRQKVLDKI DEIFVSKPER    780
KKPSGALHEE TFRKEEEFYQ SYGGKEGVLK ALELGKIRKV NGKIVKNGDM FRVDIFKHKK    840
TNKFYAVPIY TMDFALKVLP NKAVARSKKG EIKDWILMDE NYEFCFSLYK DSLILIQTKD    900
MQEPEFVYYN AFTSSTVSLI VSKHDNKFET LSKNQKILFK NANEKEVIAK SIGIQNLKVF    960
EKYIVSALGE VTKAEFRQRE DFKK                                          984

SEQ ID NO: 8              moltype = AA   length = 1393
FEATURE                   Location/Qualifiers
source                    1..1393
                          mol_type = protein
                          organism = synthetic construct
SEQUENCE: 8
MEKQRREEESS FQQPPWIPQT PMKPFSPICP YTVEDQYHSS QLEERRFVGN KDMSGLDHLS     60
FGDLLALANT ASLIFSGQTP IPTRNTEVMQ KGTEEVESLS SVSNNVAEQI LKTPEKPKRK    120
KHRPKVRREA KPKREPKPRA PRKSVVTDGQ ESKTPKRKYV RKKVEVSKDQ DATPVESSAA    180
VETSTRPKRL CRRVLDFEAE NGENQTNGDI REAGEMESAL QEKQLDSGNQ ELKDCLLSAP    240
STPKRKRSQG KRKGVQPKKN GSNLEEVDIS MAQAAKRRQG PTCCDMNLSG IQYDEQCDYQ    300
KMHWLYSPNL QQGGMRYDAI CSKVFSGQQH NYVSAFHATC YSSTSQLSAN RVLTVEERRE    360
GIFQGRQESE LNVLSDKIDT PIKKKTTGHA RFRNLSSMNK LVEVPEHLTS GYCSKPQQNN    420
KILVDTRVTV SKKKPTKSEK SQTKQKNLLP NLCRFPPSFT GLSPDELWKR RNSIETISEL    480
LRLLDINREH SETALVPYTM NSQIVLFGGG AGAIVPVTPV KKPRPRPKVD LDDETDRVWK    540
LLLENINSEG VDGSDEQKAK WWEEERNVFR GRADSFIARM HLVQGDRRFT PWKGSVVDSV    600
VGVFLTQNVS DHLSSSAFMS LASQFPVPFV PSSNFDAGTS SMPSIQITYL DSEETMSSPP    660
DHNHSSVTLK NTQPDEEKDY VPSNETSRSS SEIAISAHES VDKTTDSKEY VDSDRKGSSV    720
EVDKTDEKCR VLNLFPSEDS ALTCQHSMVS DAPQNTERAG SSSEIDLEGE YRTSFMKLLQ    780
GVQVSLEDSN QVSPNMSPGD CSSEIKGFQS MKEPTKSSVD SSEPGCCSQQ DGDVLSCQKP    840
TLKEKGKKVL KEEKKAFDWD CLRREAQARA GIREKTRSTM DTVDWKAIRA ADVKEVAETI    900
KSRGMNHKLA ERIQGFLDRL VNDHGSIDLE WLRDVPPDKA KEYLLSFNGL GLKSVECVRL    960
LTLRGHHLAFPV DTNVGRIAVR LGWVPLQPLP ESLQLHLLEM YPMLESIQKY LWPRLCKLDQ   1020
KTLYELHYQM ITFGKVFCTK SKPNCNACPM KGECRHFASA FASARLALPS TEKGMGTPDK   1080
NPLPLHLPEP FQREQGSEVV QHSEPAKKVT CCEPIIEEPA SPEPETAEVS IADIEEAFFE   1140
DPEEIPTIRL NMDAFTSNLK KIMEHNKELQ DGNMSSALVA LTAETASLPM PKLKNISQLR   1200
TEHRVYELPD EHPLLAQLEK REPDDPCSYL LAIWTPGETA DSIQPSVSTC IFPQANGMLCD   1260
EETCFSCNSI KETRSQIVRG TILIPCRTAM RGSFPLNGTY FQVNEVFADH ASSLNPINVP   1320
RELIWELPRR TVYFGTSVPT IFKGLSTEKI QACFWKGYVC VRGFDRKTRG PKPLIARLHF   1380
PASKLKGQQA NLA                                                     1393

SEQ ID NO: 9              moltype = DNA   length = 32
FEATURE                   Location/Qualifiers
source                    1..32
                          mol_type = other DNA
                          organism = synthetic construct
SEQUENCE: 9
ttggcattcc cagtgaacac aaacgttgga ag                                   32

SEQ ID NO: 10             moltype = DNA   length = 32
FEATURE                   Location/Qualifiers
source                    1..32
                          mol_type = other DNA
                          organism = synthetic construct
SEQUENCE: 10
cttccaacgt ttgtgttcac tgggaatgcc aa                                   32

SEQ ID NO: 11             moltype = DNA   length = 22
FEATURE                   Location/Qualifiers
source                    1..22
                          mol_type = other DNA
                          organism = synthetic construct
SEQUENCE: 11
tcaaaccgct atccacgccc at                                              22

SEQ ID NO: 12             moltype = DNA   length = 22
FEATURE                   Location/Qualifiers
source                    1..22
                          mol_type = other DNA
                          organism = synthetic construct
SEQUENCE: 12
attgacgtca atgggagttt gt                                              22
```

```
SEQ ID NO: 13          moltype = DNA   length = 22
FEATURE                Location/Qualifiers
source                 1..22
                       mol_type = other DNA
                       organism = synthetic construct
SEQUENCE: 13
cattgacgca aatgggcggt ag                                                   22

SEQ ID NO: 14          moltype = DNA   length = 22
FEATURE                Location/Qualifiers
source                 1..22
                       mol_type = other DNA
                       organism = synthetic construct
SEQUENCE: 14
ctctgcttat atagacctcc ca                                                   22

SEQ ID NO: 15          moltype = DNA   length = 22
FEATURE                Location/Qualifiers
source                 1..22
                       mol_type = other DNA
                       organism = synthetic construct
SEQUENCE: 15
ttccttccct ccttcgtccc ct                                                   22

SEQ ID NO: 16          moltype = DNA   length = 22
FEATURE                Location/Qualifiers
source                 1..22
                       mol_type = other DNA
                       organism = synthetic construct
SEQUENCE: 16
gcttgctagc gcccaaagcc ag                                                   22

SEQ ID NO: 17          moltype = DNA   length = 22
FEATURE                Location/Qualifiers
source                 1..22
                       mol_type = other DNA
                       organism = synthetic construct
SEQUENCE: 17
ctgagctcat tgagctgcgg ga                                                   22

SEQ ID NO: 18          moltype = DNA   length = 22
FEATURE                Location/Qualifiers
source                 1..22
                       mol_type = other DNA
                       organism = synthetic construct
SEQUENCE: 18
ccccagatga agtcgccaca ga                                                   22

SEQ ID NO: 19          moltype = DNA   length = 22
FEATURE                Location/Qualifiers
source                 1..22
                       mol_type = other DNA
                       organism = synthetic construct
SEQUENCE: 19
tgcgacaagg gataaaccat tt                                                   22

SEQ ID NO: 20          moltype = DNA   length = 22
FEATURE                Location/Qualifiers
source                 1..22
                       mol_type = other DNA
                       organism = synthetic construct
SEQUENCE: 20
ccagggacca gctgccgtgt gg                                                   22

SEQ ID NO: 21          moltype = RNA   length = 73
FEATURE                Location/Qualifiers
source                 1..73
                       mol_type = other RNA
                       organism = synthetic construct
SEQUENCE: 21
gttttagtcc ctgaaaaggg actaaaataa agagtttgcg ggactctgcg gggttacaat          60
cccctaaaac cgc                                                             73
```

-continued

```
SEQ ID NO: 22           moltype = DNA  length = 73
FEATURE                 Location/Qualifiers
source                  1..73
                        mol_type = other DNA
                        organism = synthetic construct
SEQUENCE: 22
gttttagtcc ctgaaaaggg actaaaataa agagtttgcg ggactctgcg gggttacaat   60
ccctaaaac cgc                                                       73

SEQ ID NO: 23           moltype = AA  length = 25
FEATURE                 Location/Qualifiers
source                  1..25
                        mol_type = protein
                        organism = synthetic construct
SEQUENCE: 23
SPKKKRVEAS KLGGGGGGGG SGSVD                                         25

SEQ ID NO: 24           moltype = AA  length = 10
FEATURE                 Location/Qualifiers
source                  1..10
                        mol_type = protein
                        organism = synthetic construct
SEQUENCE: 24
SPKKKRVEAS                                                          10

SEQ ID NO: 25           moltype = AA  length = 15
FEATURE                 Location/Qualifiers
source                  1..15
                        mol_type = protein
                        organism = synthetic construct
SEQUENCE: 25
GGGGSGGGGS GGGGS                                                    15

SEQ ID NO: 26           moltype = AA  length = 5
FEATURE                 Location/Qualifiers
source                  1..5
                        mol_type = protein
                        organism = synthetic construct
SEQUENCE: 26
GSSGN                                                               5

SEQ ID NO: 27           moltype = AA  length = 6
FEATURE                 Location/Qualifiers
source                  1..6
                        mol_type = protein
                        organism = synthetic construct
SEQUENCE: 27
GGGSGG                                                              6

SEQ ID NO: 28           moltype = AA  length = 8
FEATURE                 Location/Qualifiers
source                  1..8
                        mol_type = protein
                        organism = synthetic construct
SEQUENCE: 28
GPKKKRKV                                                            8

SEQ ID NO: 29           moltype = AA  length = 8
FEATURE                 Location/Qualifiers
source                  1..8
                        mol_type = protein
                        organism = synthetic construct
SEQUENCE: 29
DYKDDDDK                                                            8

SEQ ID NO: 30           moltype = AA  length = 21
FEATURE                 Location/Qualifiers
source                  1..21
                        mol_type = protein
                        organism = synthetic construct
SEQUENCE: 30
GGGGGGSGGG GGGGGGGGGG G                                             21
```

```
SEQ ID NO: 31           moltype = DNA  length = 19
FEATURE                 Location/Qualifiers
source                  1..19
                        mol_type = other DNA
                        organism = synthetic construct
SEQUENCE: 31
gaagtcattg aggcctgct                                                      19

SEQ ID NO: 32           moltype = DNA  length = 22
FEATURE                 Location/Qualifiers
source                  1..22
                        mol_type = other DNA
                        organism = synthetic construct
SEQUENCE: 32
atcatccaac agcttccgcg ca                                                  22
```